US005869719A

United States Patent [19]
Patton

[11] Patent Number: 5,869,719
[45] Date of Patent: *Feb. 9, 1999

[54] TRANSGENIC PLANTS HAVING INCREASED BIOTIN CONTENT

[75] Inventor: David A. Patton, Durham, N.C.

[73] Assignee: Novartis Finance Corporation, New York, N.Y.

[ * ] Notice: The term of this patent shall not extend beyond the expiration date of Pat. No. 5,859,335.

[21] Appl. No.: 846,338

[22] Filed: Apr. 30, 1997

Related U.S. Application Data

[63] Continuation-in-part of Ser. No. 401,068, Mar. 8, 1995, Pat. No. 5,859,335.
[51] Int. Cl.⁶ ............................... A01H 5/00; C12N 5/04
[52] U.S. Cl. ................. 800/278; 435/253.31; 435/240.4; 435/121; 536/23.6; 536/23.7
[58] Field of Search ........................... 435/252.31, 240.4, 435/121, 69.1, 69.8, 172.3; 800/205, DIG. 15, 17, DIG. 26, 43, DIG. 58, 58; 536/23.6, 23.7

[56] References Cited

U.S. PATENT DOCUMENTS

| | | | |
|---|---|---|---|
| 5,096,823 | 3/1992 | Gloeckler et al. | ................. 435/252.31 |
| 5,258,300 | 11/1993 | Glassman et al. | ................... 435/240.4 |
| 5,445,952 | 8/1995 | Campbell et al. | ...................... 435/121 |

FOREIGN PATENT DOCUMENTS

| | | |
|---|---|---|
| 0635572 | 6/1994 | European Pat. Off. . |
| 2216530 | 10/1989 | United Kingdom . |
| WO 94/08023 | 4/1994 | WIPO . |

OTHER PUBLICATIONS

Altschul, S.F. et al., "Basic Local Alignment Search Tool", *J. Mol. Biol.* 215:403–410 (1990).
Baldet, P. et al., "Biotin biosynthesis in higher plant cells Identification of intermediates" *Eur. J. BioChem* 217:479–485 (1993).
Baldet et al., Genbank Access. No. L34413, Locus ATH-SEACA, (01 Jan. 1995).
Dickson et al., "Genetic Regulation: The Lac Control Region", *Science* 187:27–35 (1975).
Eisenberg, M.A., "Biotin: Biogenesis, Transport, and Their Regulation", *Adv. Enzymol.* 38:317–372 (1973).
Eisenberg, M.A., "Regulation of the Biotin Operon in *E. coli*", *Ann. N.Y. Acad. Sci.* 447:335–349 (1985).
Frigg, M., "Available Biotin Content of Various Feed Ingredients", *Poultry Science* 63:750–753 (1983).
Gerbling et al., "A new Acyl–CoA Synthetase, Located in Higher Plant Cytosol", *J. Plant Physiol.*, 143:561–564 (1994).
Gloeckler, R. et al., "Cloning and characterization of the *Bacillus sphaericus* genes controlling the bioconversion of pimelate into dethiobiotin", *Gene* 87:63–70 (1990).
Knowles, J.R., "The Mechanism of Biotin–Dependent Enzymes", *Ann. Rev. BioChem.* 58:195–221 (1989).

Kopinski, J.S. et al., "Biotin studies in pigs. 1. Biotin deficiencey in the young pig", *British Journal of Nutrition* 62:751–759 (1989).
Kopinski, J.S. et al., "Biotin in Animal Nutrition", *Nutrition Reviews* 48:352–355 (1990).
Levy–Schil, S. et al., "Biotin biosynthetic pathway in recombinant strains of *Escherichia coli* overexpressing bio genes: evidence for a limiting step upstream from KAPA", *Appl. Microbiol. Biotechnol.* 38:755–762 (1993).
Marshall, M.W., "The Nutritional Importance of Biotin–An Update", *Nutrition Today* Article 3:26–29 (1987).
Newman, T. et al., "Genes Galore: A Summary of Methods for Accessing Results from Large–Scale Partial Sequencing of Anonymous *Arabidopsis* cDNA Clones", *Plant Physiol.* 106:1241–1255 (1994).
Otsuka, A.J. et al., "The *Escherichia coli* Biotin Biosynthetic Enzyme Sequences Predicted from the Nucleotide Sequence of the bio Operon", *The Journal of Biological Chemistry* 263:19577–19585 (1988).
Pai, C.H., "Mutant of *Escherichia coli* with Derepressed Levels of the Biotin Biosynthetic Enzymes", *J. Bacteriol.* 112: 1280–1287 (1972).
Patton et al., "Complementation of an *Arabidosis thaliana* biotin auxotroph with an *Escherichia coli* biotin biosynthetic gene", *Mol. Gen. Genet.*, 251:261–266 (1966).
Patton et al., "Biotin Synthase from *Arabidopsis thaliana*", *Plant Physiol.* 112:371–378 (1996).
Robel, E.J., "The Value of Supplemental Biotin for Increasing Hatchability of Turkey Eggs", *Poultry Science* 70:1716–1722 (1991).
Sakurai, N. et al., "Improvement of d–biotin–hyperproducing combinant strain of *Serratia marcescens*" *J. Biotech.* 36:63–73 (1994).
Shellhammer, A.J. Jr., "Analysis of a Biotin Auxotroph of *Arabidopsis Thaliana*", *Oklahoma State University Thesis* 1–134 (1986).
Shiuan, D. et al., "Transcriptional regulation and gene arrangement of *Escherichia coli, Citrobacter freundil* and *Salmonella typhimurium* biotin operons", *Gene* 67:203–211 (1988).

(List continued on next page.)

*Primary Examiner*—Douglas W. Robsinson
*Assistant Examiner*—Ousama M-Faiz Zaghmout
*Attorney, Agent, or Firm*—J. Timothy Meigs

[57] ABSTRACT

The present invention reveals that biotin biosynthesis in a plant is enhanced when the level of one or more of the enzymes in the plant biotin biosynthetic pathway is increased. Based upon this revelation, methods that increase the level of one or more biotin biosynthetic enzymes in plant tissue are provided as a means for achieving enhanced levels of biotin in plant tissue. In particular, a method is provided for enhancing biotin levels by introducing into plant tissue a chimeric gene capable of expressing a biotin biosynthetic enzyme such as biotin synthase. Thus, transgenic plant tissue, including whole plants, having enhanced levels of biotin is likewise provided.

13 Claims, 4 Drawing Sheets

OTHER PUBLICATIONS

Stryer, L., "Amino Acid Biosynthesis is Regulated by Feedback Inhibition", *BioChemistry* 2:505–503 (1981).

Van den Broeck et al., "Targeting of a foreign protein to chloroplasts by fusion to the transit peptide from the small subunit of ribulose 1,5–bisphosphate carboxylase", *Nature*, 313:358–363 (1985).

Watanabe, K. et al., "The Selection of Cultured Plant Cell Lines Producing High Levels of Biotin", *Phytochemistry* 21:513–516 (1982).

Wolfner, M. et al.,"Integration of Amino Acid Biosynthesis into the Cell Cycle of *Saccharomyces cerevisiae*", *J. Mol. Biol.* 96:273.

Wu, A. et al., "Transcription termination: Nucleotidee sequence at 3'end of tryptophan operon in *Escherichia coli*", *Proc. Nat. Acad. Sci. U.S.* 75:5442 (1978).

Itoh et al., "Silcing of Waxygenes in rice containing WX transgenes", Mol. Gen. Genet. 1997. 255:351–358.

Finnegan and McElroy., "Transgene inactivation: plants fight back." Bio/Technology. 1994. vol. 12:883–888.

Figure 2

```
A.t.    1 MMLVRSVFRSQLRPSVSGGLQSASCYSSLSAASAEAERTIREGPRNDWSR 50
                                              :.|   |.
E.c.    1 ..........................MAHRPRWTL  9

51 DEIKSVYDSPLLDLLFHGAQVHRHVHNFREVQQCTLLSIKTGGCSEDCSY 100
          .::...:::.||||||.:.||||:  : |:|| :|||||||||:|.|||.|
       10 SQVTELFEKPLLDLLFEAQQVHRQHFDPRQVQVSTLLSIKTGACPEDCKY 59

101 CPQSSRYSTGVKAQRLMSKDAVIDAAKKAKEAGSTRFCMGAAWRDTIGRK 150
          |||.|||.||:.|:|||. ..|::.|:|||.||||||||||||::. :|.
       60 CPQTSRYKTGLEAERLMEVEQVLESARKAKAAGSTRFCMGAAWKNPHERD 109

151 TNFSQILEYIKEIRGMGMEVCCTLGMIEKQQALELKKAGLTAYNHNLDTS 200
          : : :  :.::::||:|.| ||| :.. || | .|||. ||||||||
      110 MPYLEQM..VQGVKAMGLEACMTLGTLSESQAQRLANAGLDYYNHNLDTS 157

201 REYYPNVITTRSYDDRLETLSHVRDAGINVCSGGIIGLGEAEEDRIGLLH 250
          .|:|.:||||.|::||:||..||||||.|||||||:||||. .|| |||
      158 PEFYGNIITTRTYQERLDTLEKVRDAGIKVCSGGIVGLGETVKDRAGLLL 207

251 TLATLPSHPESVPINALLAVKGTPLEDQKPVEIWEMIRMIGTARIVMPKA 300
          ||.||..|||||||| |: ||||||.|...|: :::|| |:.|||:||..
      208 QLANLPTPPESVPINMLVKVKGTPLADNDDVDAFDFIRTIAVARIMMPTS 257

301 MVRLSAGRVRFSMSEQALCFLAGANSIFTGEKLLTTPNNDFDADQLMFKT 350
          |||||| .:. .||:||:|||||||| |||||||| : || :|:.
      258 YVRLSAGREQMNEQTQAMCFMAGANSIFYGCKLLTTPNPEEDKDLQLFRK 307

351 LGLIPKPPSFSGDDSESENCEKVASASH*........... 379
          ||| |..... ::|.| :.  . |  ..
      308 LGLNPQQTAVLAGDNEQQQRLEQALMTPDTDEYYNAAAL* 347
```

TRANSGENIC PLANTS HAVING INCREASED BIOTIN CONTENT

This is a continuation-in-part of U.S. Ser. No. 08/401,068, filed 8 Mar. 1995 now U.S. Pat. No. 585,933.

FIELD OF THE INVENTION

The invention relates generally to methods for enhancing the nutritional value of plants as a food source for humans and animals. In particular, the invention relates to the application of genetic engineering techniques to achieve plants and plant tissue with enhanced biotin production.

BACKGROUND OF THE INVENTION

I. Biotin Biosynthesis

Biotin (vitamin H) is an essential nutrient for all living organisms (Eisenberg, M. A., *Adv. Enzymol.* 38: 317–372 (1973)). It is a basic component of cell metabolism that acts as a cofactor that binds covalently to carboxylases to facilitate the transfer of carboxyl groups during enzymatic carboxylation, decarboxylation and transcarboxylation reactions (Knowles, J. R., *Ann. Rev. BioChem.* 58: 195–221 (1989)). The chemical structure of the naturally occurring d-isomer of biotin is as follows:

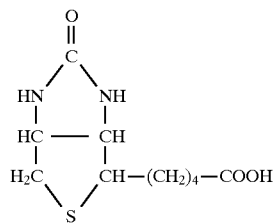

Biotin biosynthesis has been extensively studied in microorganisms, primarily through the isolation and characterization of biotin auxotrophic mutants (Eisenberg, supra). Through this work, four enzymatic steps common to *E. coli* and other microorganisms for the biosynthesis of biotin from the precursor pimeloyl-CoA have been elucidated (Eisenberg, supra; Pai, C. H., *Canad. J. Microbiol.* 15: 21–26 (1969); del Campillo-Campbell et al., *J. Bacteriol.* 94: 2065–2066 (1967)). Analysis of two classes of *E. coli* mutants, those defective in either the bioC (SEQ ID NO:11) or the bioH gene, suggests that the products of these genes play a role in biotin synthesis, but at steps prior to pimeloyl-CoA. The final common steps of the biotin biosynthetic pathway are as follows:

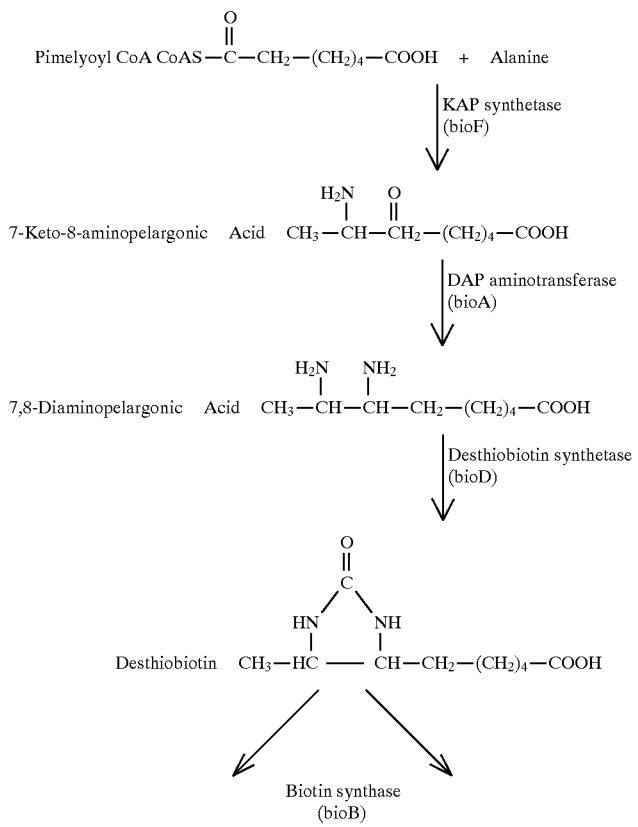

-continued

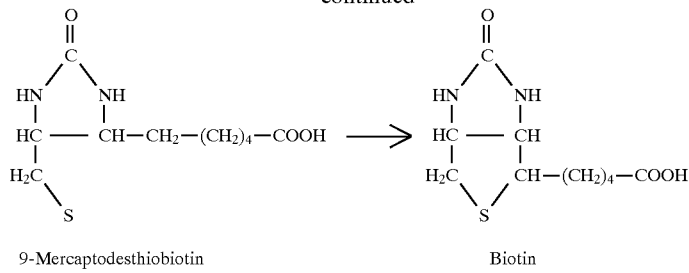

9-Mercaptodesthiobiotin                    Biotin

The first step in this common biotin biosynthetic pathway is the synthesis of 7-keto-8aminopelargonic Acid (KAP) from pimeloyl-CoA and L-alanine. This step is catalyzed by an enzyme known as KAP synthetase, which is encoded by the bioF gene in *E. coli* (Eisenberg, supra). This gene is part of the *E. coli* biotin operon, which has been cloned and sequenced (Otsuka, A. J. et al., *J. Biol. Chem.* 263: 19577–19585 (1988); Genbank accession no. J04423).

The second step in this common biotin biosynthetic pathway is the conversion of KAP into 7,8-Diaminopelargonic Acid (DAP). This step is catalyzed by an enzyme known as DAP aminotransferase, which is encoded by the bioA gene (Eisenberg and Stoner, in *Methods in Enzomology* 62: 342–347, ed. by McCormick and Wright, pub. by Acad. Press, NY (1979); Stoner and Eisenberg, *J. Biol. Chem.* 250: 4037–4043 (1975); Stoner and Eisenberg, *J. Biol. Chem.* 250: 4029–4036 (1975); Eisenberg, supra; Eisenberg and Stoner, *J. Bacteriol.* 108: 1135–1140 (1971); Pai, C. H., *J. Bacteriol.* 105: 793–800 (1971)). The bioA gene is also part of the *E. coli* biotin operon, which has been cloned and sequenced (Otsuka, A. J. et al., supra.; Genbank accession no. J04423).

The third step in this common biotin biosynthetic pathway is the conversion of DAP into desthiobiotin. This step is catalyzed by an enzyme known as desthiobiotin synthetase, which is encoded by the bioD gene (Eisenberg, M. A., *Ann. N.Y. Acad. Sci.* 447: 335–349 (1985); Cheeseman and Pai, *J. Bacteriol.* 104: 726–733 (1970); Eisenberg and Krell, *J. Biol. Chem.* 244: 5503–5509 (1969); Pai, C. H., *J. Bacteriol.* 99: 696–701 (1969)). The bioD gene is also part of the *E. coli* biotin operon, which has been cloned and sequenced (Otsuka, A. J. et al., supra.; Genbank accession no. J04423).

The final step in this common biotin biosynthetic pathway involves the addition of sulfur to desthiobiotin and subsequent ring closure to form biotin. These steps are catalyzed by an enzyme known as biotin synthase, which is encoded by the bioB gene (Eisenberg, M. A., *Ann. N.Y. Acad. Sci.* 447: 335–349 (1985); Pai, C. H., *J. Bacteriol.* 112: 1280–1287 (1972)).

The biotin biosynthetic pathway in plant cells has also been elucidated (Baldet, P. et al., *Eur. J. BioChem* 217: 479–485 (1993)). This pathway is very similar to the pathway common to all microorganisms, which is described above, with two additional steps. First, the pathway in plants includes the conversion of pimelic acid to pimeloyl-CoA. This step is catalyzed by an enzyme known as pimeloyl-CoA synthetase. This step may also occur in a number of microorganisms, although it may not be common to all (Gloeckler, R. et al., *Gene* 87: 63–70 (1990); Eisenberg, M., in "Escherichia coli and Salmonella typhimurium. Cellular and Molecular Biology", pp. 544–550, ed. by Neidhardt, F. C. et al., pub. by Amer. Soc. Microbiol., NY (1987); Izumi, Y. et al., in Methods in Enzomology 62: 327–330, ed. by McCormick and Wright, pub. by Acad. Press, NY (1979); Izumi, Y. et al., *BioChem. Biopys. Acta* 264: 210–213 (1972)).

Secondly, the conversion of desthiobiotin to biotin involves the creation of an intermediate compound, 9-mercaptodesthiobiotin (Baldet et al., supra). This intermediate may also occur in microorganisms, as conversion of desthiobiotin into biotin in these organisms is not completely understood and as this compound will support the growth of *E. coli* bioB mutants (Baldet et al, supra).

II. Biotin as a Nutrient

For higher eukaryotic organisms other than plants and some fungi, biotin is an essential vitamin that must be part of the diet. Biotin deficiencies in animals can have a number of adverse effects, including a reduction in growth rate, alopecia (hair loss), scaly dermatitis, and edema and erythema of the feet (*Nutritional Reviews* 48: 352–355 (1990); Kopinski, J. S. et al., *J. Nutrition* 62: 751–759 (1989); *Poultry Science* 67: 590–595 (1988); Marshall, M. W., *Nutrition Today* 22–23: 26–29 (1987)). In humans, biotin deficiency has also been associated with a number of genetic and acquired diseases (Marshall, M. W., supra).

In general, plant-based feeds do not contain enough biotin to serve as a sufficient dietary source of this vitamin. This is especially true for stockyard animals such as pigs and chickens (Frigg, M., *Poultry Science* 63: 750–753 (1983). Enhanced performance has been observed in a number of production animals following biotin supplementation of the normal diet (Kopinski, J. S. et al. *British Journal of Nutrition* 62:751–789)). As a result, additional biotin is incorporated as a feed supplement into the diet of many animals (Robel, E. J., *poultry Science* 70: 1716–1722 (1991)).

If biotin production in plants could be increased, the need for additional biotin in animal and human diets from sources other than plants could be reduced or eliminated. However, until the present invention, not enough was known about this pathway in plants, or its regulation, to achieve the objective of increasing biotin production in plants.

One approach for enhancing biotin production that might be considered would be to alter the levels of intermediates or enzymes in the biotin biosynthetic pathway. However, in light of what was previously known, this approach would not have been expected to work because metabolic pathways are typically tightly regulated so that metabolite synthesis remains stable despite fluctuations that may occur in the levels of available pathway intermediates and enzymes. Regulation of metabolite synthesis may involve a variety of mechanisms. Classic examples of mechanisms used to regulate metabolite synthesis in microorganisms include catabolite repression and enzyme induction (Dickson et al. *Science* 187:27–35 (1975)), feedback inhibition (Stryer, L., "BioChemistry", 2nd ed., pub. by W. H. Freeman and Co., San Francisco, pp. 500–503 (1981)), attenuation (Wu, A. and Platt, T. *Proc. Nat. Acad. Sci. U.S.* 75:5442 (1978)), and general control (M. Wolfner et al. *J. Mol. Biol.* 96:273–290) ). Some or all of these mechanisms may also be involved in metabolic pathway regulation in plants. Because these pathways are typically tightly regulated through a variety of mechanisms, the effect that increasing the amount of any one enzyme in a pathway would have, if any, upon the final level of the end product (metabolite) synthesized could not ordinarily be predicted.

SUMMARY OF THE INVENTION

The present invention is based upon the discovery that biotin levels in plants may be enhanced simply by increasing the levels of one or more of the enzymatic activities in the plant biotin biosynthetic pathway. This discovery therefore reveals an exception to what was previously known about metabolic pathway regulation in plants. The inventor has utilized this discovery to develop a general approach for predictably increasing the levels of biotin produced in plants to enhance their nutritional value as a dietary source of biotin.

Accordingly, a method is provided for enhancing biotin levels in a plant by introducing a chimeric gene into the plant that expresses an enzyme in the plant biotin biosynthetic pathway. The enzyme that may be expressed according to this aspect of the invention includes, but is not limited to, a pimeloyl-CoA synthetase, a KAP synthetase, a DAP aminotransferase, a desthiobiotin synthetase, and a biotin synthase. In a preferred embodiment, enhancement of biotin levels in a plant is achieved by expressing a biotin synthase in the plant. The chimeric gene may encode an enzyme from a non-plant source such as a microorganism (e.g. bacteria), although an enzyme from a plant source is preferred. Furthermore, multiple chimeric genes encoding more than one enzyme in the plant biotin biosynthetic pathway may be introduced into the plant to achieve an even greater enhancement of biotin levels.

In another aspect of the invention, transgenic plant tissue, including plants, seeds, and cultured tissue, with enhanced biotin levels is provided that comprises one or more chimeric genes expressing enzyme(s) in the plant biotin biosynthetic pathway including, but not limited to, a pimeloyl-CoA synthetase, a KAP synthetase, a DAP aminotransferase, a desthiobiotin synthetase, and a biotin synthase. In a preferred embodiment, the transgenic plant tissue comprises a chimeric gene expressing a biotin synthase. This plant tissue may be used as an improved dietary source of biotin.

DESCRIPTION OF THE SEQUENCES IN THE SEQUENCE LISTING

SEQ ID NO:1: Nucleotide sequence of the *E. coli* KAP synthetase gene.
SEQ ID NO:2: Amino acid sequence of the *E. coli* KAP synthetase encoded by SEQ ID NO:1.
SEQ ID NO:3: Nucleotide sequence of the *E. coli* DAP aminotransferase gene.
SEQ ID NO:4: Amino acid sequence of the *E. coli* DAP aminotransferase encoded by SEQ ID NO:3.
SEQ ID NO:5: Nucleotide sequence of the *E. coli* desthiobiotin synthetase gene.
SEQ ID NO:6: Amino acid sequence of the *E. coli* desthiobiotin synthetase encoded by SEQ ID NO:5.
SEQ ID NO:7: Nucleotide sequence of the *E. coli* biotin synthetase (bioB) gene.
SEQ ID NO:8: Amino acid sequence of the *E. coli* biotin synthetase (BioB enzyme) encoded by SEQ ID NO:7.
SEQ ID NO:9: Forward PCR primer used in Example 1.
SEQ ID NO:10: Reverse PCR primer used in Example 1.
SEQ ID NO:11: Nucleotide sequence of the *E. coli* bioC gene.
SEQ ID NO:12: Amino acid sequence of the *E. coli* BioC enzyme encoded by SEQ ID NO:11.
SEQ ID NO:13: Nucleotide sequence of the *Arabidopsis thaliana* biotin synthase gene BIO2.
SEQ ID NO:14: Amino acid sequence of the *Arabidopsis thaliana* BIO2 enzyme encoded by SEQ ID NO:11.
SEQ ID NO:15: Forward PCR primer DP199 used in Example 9.
SEQ ID NO:16: Reverse PCR primer DP200 used in Example 9.
SEQ ID NO:17: Forward PCR primer DP201 used in Example 9.
SEQ ID NO:18: Reverse PCR primer DP202 used in Example 9.
SEQ ID NO:19: Forward PCR primer DP205 used in Example 9.
SEQ ID NO:20: Reverse PCR primer DP206 used in Example 9.

The *E. coli* bioA gene is cloned as a 1.3 kb EcoRI fragment between the double 35S promoter (2×35S) and the tml terminater (tml 3') of pCGN1761. This 4.3 kb XbaI expression cassette is cloned into the XbaI site pCIB200. Expression of the kanamycin resistance gene (Tn5 neo) in the T-DNA portion of pCIB200 is directed by the nopaline synthase promoter (nos) and terminator (nos 3'). Direction of transcription is denoted by horizontal arrows. Restriction recognition sites XbaI (B), XhoI (X), and EcoRI (E) are shown at their approximate position with vertical arrows.

FIG. 2: Comparison of the *E. coli* BioB protein and the protein encoded by the *Arabidopsis* BIO2 cDNA clone (NRRL #B-21398)

This figure provides a comparison of the deduced amino acid sequence encoded by the *Arabidopsis thaliana* BIO2 cDNA (A.t. -SEQ ID NO:14) and the *E. coli* BioB amino acid sequence (E.c. -SEQ ID NO:8).

Figure 3:
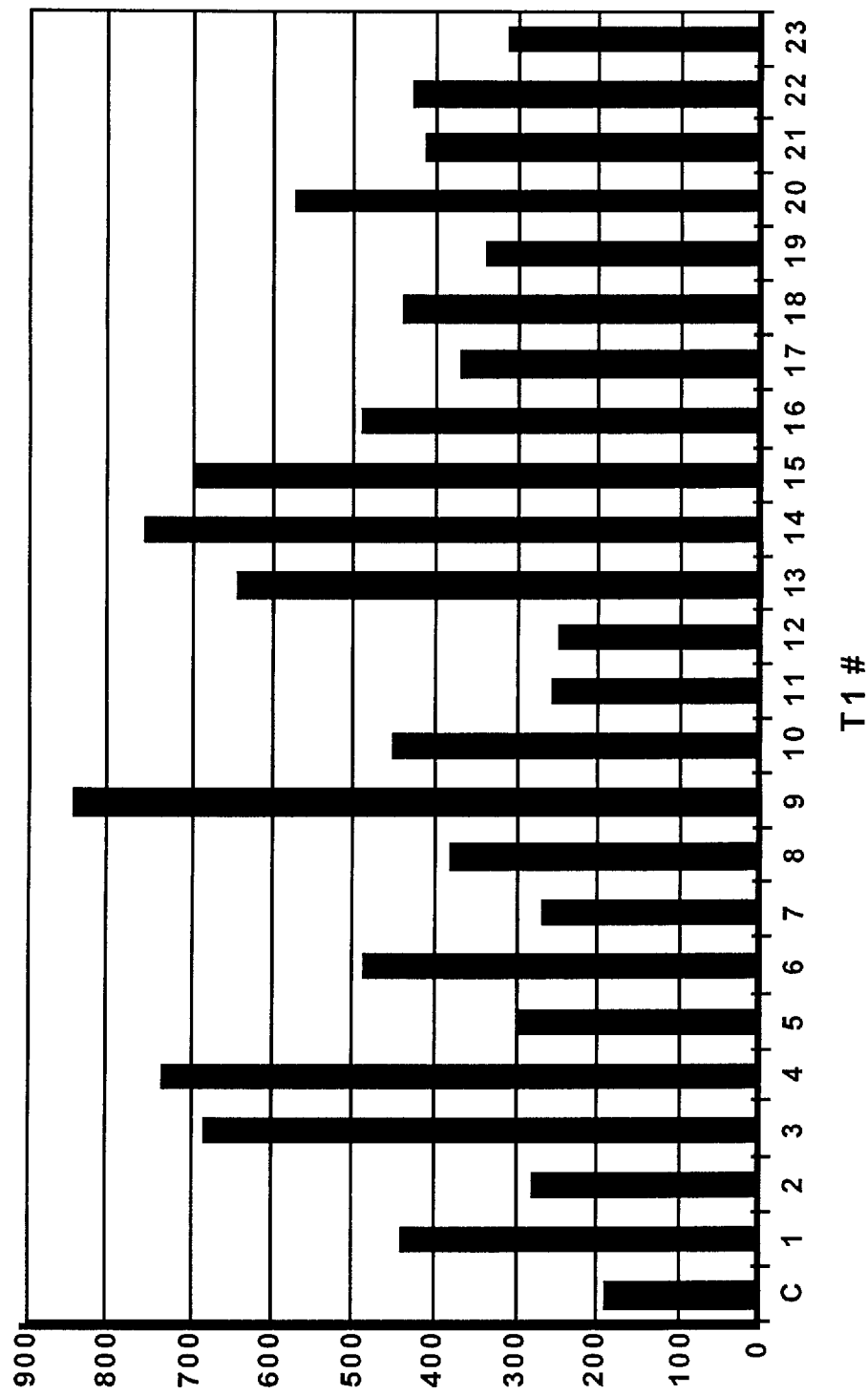

FIG. 3: Biotin Content in Arabidopsis Transformed with 2S-2 Driven *E. coli* bioB gene This graph shows picograms of biotin per silique for each transformed T1 Arabidopsis line.

Figure 4:
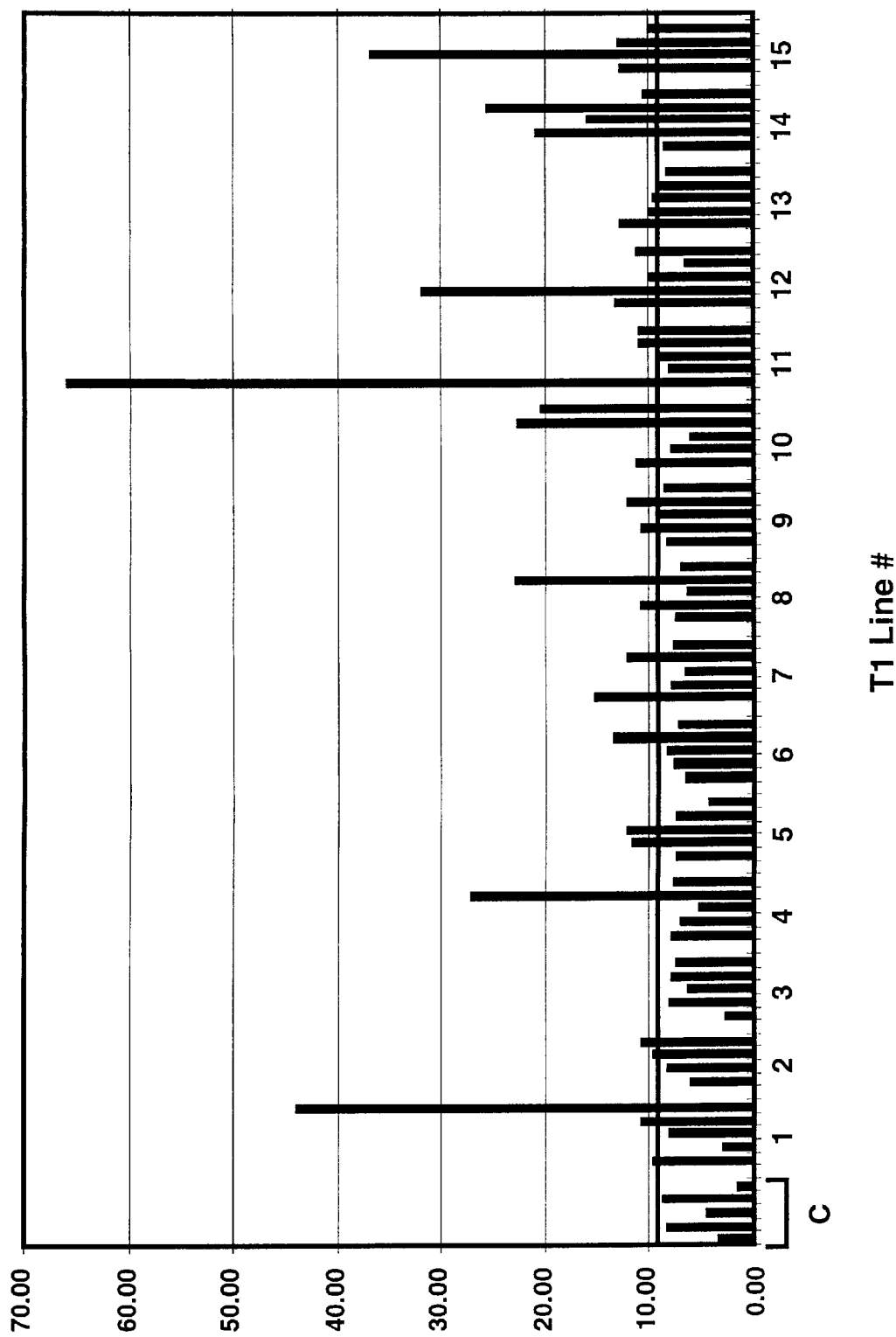

FIG. 4: Biotin Content in Arabidopsis Transformed with 35-S Driven Arabidopsis BIO2 gene This graph shows the biotin content in leaves of several T2 plants from each transformed T1 Arabidopsis line in picograms per milligram (pg/mg) Fresh Weight.

DETAILED DESCRIPTION OF THE INVENTION

The present invention provides a general approach for predictably enhancing biotin biosynthesis in plant tissue, thereby enhancing the nutritional value of such tissue as a dietary source of biotin. According to the present invention, the amount of biotin in plant tissue may be increased by increasing the amount of one or more biotin biosynthetic enzymes present in such tissue.

For purposes of the present invention, the term "plant tissue" is intended to include plants, seeds, progeny thereof, cultured plant cells and any other tissue of plant origin.

For purposes of the present invention, a "biotin biosynthetic enzyme" (BBE) is defined as an enzyme that catalyzes one or more of the steps required for the conversion of pimelic acid into biotin in a plant. Biotin biosynthetic enzymes include, but are not necessarily limited to, a pimeloyl-CoA synthetase, a KAP synthetase, a DAP aminotransferase, a desthiobiotin synthetase, an enzyme that converts desthiobiotin to 9mercaptodesthiobiotin, and a biotin synthase. Natural sources of biotin biosynthetic enzymes and the genes encoding them include plants and microbes.

The amount of a biotin biosynthetic enzyme present in a plant or plant cell may be increased using any suitable means. In particular, this may be accomplished by introducing into the plant or plant cell a chimeric gene capable of expressing a biotin biosynthetic enzyme in a plant cell. Such a chimeric gene will comprise a promoter capable of regulating gene expression in a plant, operably linked to a DNA sequence that encodes a biotin biosynthetic enzyme, followed by a transcriptional terminator and polyadenylation signal.

DNA molecules encoding biotin biosynthetic enzymes from *E. coli*, *Bacillus sphaericus*, *Bacillus subtilis* and *Serratia marcescens* are generally available (see U.S. Pat. No. 5,096,823 issued Mar. 17, 1992 to Gloeckler et al.; Otsuka, A. J. et al., *J. Biol. Chem*. 263(36): 19577–19585 (1988); European Patent Application no. 94108998.9 published Jan. 25, 1995 as pub. no. 635,572 to Bower, S. G. et al., Sakurai, N. et al., *J. Biotech*. 36: 63–73 (1994); see also genbank accession no. D17468 for the *Serratia marcescens* biotin operon sequence. The *E. coli* coding sequence and corresponding amino acid sequence for KAP synthetase are provided in SEQ ID NOS:1 and 2, respectively. The *E. coli* coding sequences and corresponding amino acid sequence for DAP aminotransferase is provided in SEQ ID NOS:3 and 4, respectively. The *E. coli* coding sequence and corresponding amino acid sequence for desthiobiotin synthetase are provided in SEQ ID NOS:5 and 6, respectively. The *E. coli* coding sequence and corresponding amino acid sequence for biotin synthase are provided in SEQ ID NOS:7 and 8, respectively. The *E. coli* coding sequence and corresponding amino acid sequence for the bioC gene are provided in SEQ ID NOS:11 and 12, respectively. The bioC gene encodes a protein that is involved in biotin biosynthesis at a step prior to the synthesis of 7-keto-8-aminopelargonic Acid (KAP) from pimeloyl-CoA and L-alanine, which is catalyzed by an enzyme known as KAP synthetase. The Arabidopsis cDNA and encoded amino acid sequences for biotin synthase are provided in SEQ ID NOS:13 and 14, respectively.

DNA molecules encoding biotin biosynthetic enzymes may also be isolated from any plant species desired by applying standard molecular biological techniques. One suitable approach that has been successfully used to isolate a variety of biosynthetic genes in other metabolic pathways from higher eukaryotes is the complementation of microbial mutants deficient in the activity of interest (see, e.g. U.S. patent application Ser. No. 08/061,644 to Ward et al., incorporated by reference herein in its entirety (histidine biosynthetic genes); Frisch et al., *Mol. Gen. Genet*. 228: 287 (1991) (lysine biosynthetic genes); Aimi et al., *J. Biol. Chem*. 265: 9011 (1990)(purine biosynthetic genes); and Niyogi et al., *Plant Cell* 5: 1011 (1993) (tryptophan biosynthetic genes)). For this approach, a library of cDNAs from a plant of interest is cloned in a vector that can direct expression of the cDNA in the microbial host. The vector is then transformed or otherwise introduced into a microbe deficient in the activity of interest, and colonies are selected that are phenotypically no longer mutant. Suitable microbial host organisms that are deficient in the various biotin biosynthetic enzymatic activities are readily available in the art for use in this method (del Campillo-Campbell et al., *J. Bacteriol*. 94: 2065–2066 (1967); Pai C. H. *Canad. J. Micriobiol*. 15: 21–26 (1969); Cleary and Campbell, *J. Bacteriol*. 112: 830–839 (1972)).

Alternatively, plant or other microbial coding sequences for biotin biosynthetic enzymes may be isolated according to well known techniques based on their sequence homology to the known microbial biotin biosynthetic coding sequences. In these techniques, all or part of a known biotin biosynthetic coding sequence is used as a probe that selectively hybridizes to corresponding biotin biosynthetic coding sequences present in population of cloned genomic DNA fragments or cDNA fragments (i.e. genomic or cDNA libraries) from the chosen plant. Such techniques include hybridization screening of plated DNA libraries (either plaques or colonies; see, e.g. Sambrook et al., *Molecular Cloning*, eds., Cold Spring Harbor Laboratory Press. (1989)) and amplification by PCR using oligonucleotide primers corresponding to sequence domains conserved among known amino acid sequences of the particular biotin biosynthetic enzymes (see, e.g. Innis et al.,. *PCR Protocols, a Guide to Methods and Applications* eds., Academic Press (1990)).

Coding sequences for biotin biosynthetic enzymes may be genetically engineered for optimal expression in a particular crop plant. Methods for modifying coding sequences to achieve optimal expression in a particular crop species are well known (see, e.g. Perlak et al., *Proc. Natl. Acad. Sci. USA* 88: 3324 (1991); Koziel et al., *Bio/technol*. 11: 194 (1993)).

A DNA sequence coding for a biotin biosynthetic enzyme may be inserted into an expression cassette designed for plants to construct a chimeric gene according to the invention using standard genetic engineering techniques. The choice of specific regulatory sequences such as promoter, signal sequence, 5' and 3' untranslated sequences, and enhancer appropriate for the achieving the desired pattern and level of expression in the chosen plant host is within the level of skill of the routineer in the art. The resultant molecule, containing the individual elements linked in proper reading frame, may be inserted into a vector capable of being transformed into a host plant cell.

Examples of promoters capable of functioning in plants or plant cells (i.e., those capable of driving expression of associated coding sequences such as those coding for biotin biosynthetic enzymes in plant cells) include the cauliflower mosaic virus (CaMV) 19S or 35S promoters and CaMV double promoters; nopaline synthase promoters; pathogenesis-related (PR) protein promoters; small subunit of ribulose bisphosphate carboxylase (ssuRUBISCO) promoters, and the like. Preferred are the rice actin promoter (McElroy et al., *Mol. Gen. Genet*. 231: 150 (1991)), maize ubiquitin promoter (EP 0 342 926; Taylor et al., *Plant Cell Rep*. 12: 491 (1993)), and the PR-I promoter from tobacco, Arabidopsis, or maize (see U.S. Pat. No. 5,614,395 to Ryals, incorporated by reference herein in its entirety). Also preferred are the 35S promoter and an enhanced or double 35S promoter such as that described in Kay et al., *Science* 236: 1299–1302 (1987) and the double 35S promoter cloned into pCGN2113, deposited as ATCC 40587, which are disclosed in U.S. Pat. No. 5,614,395. The promoters themselves may be modified to manipulate promoter strength to increase expression of the associated coding sequence in accordance with art-recognized procedures. Preferred promoters for use with the present invention are those that confer high level constitutive expression or, more preferably, those that confer specific high level expression in the tissues incorporated into the diet of animals or humans.

Signal or transit peptides may be fused to the BBE coding sequence in the chimeric DNA constructs of the invention to direct transport of the expressed BBE to the desired site of action. Examples of signal peptides include those natively linked to the plant pathogenesis-related proteins, e.g. PR-1, PR-2, and the like. See, e.g., Payne et al., *Plant Mol. Biol.* 11:89–94 (1988). Examples of transit peptides include the chloroplast transit peptides such as those described in Von Heijne et al., *Plant Mol. Biol. Rep.* 9:104–126 (1991); Mazur et al., *Plant Physiol.* 85: 1110 (1987); Vorst et al., *Gene* 65: 59 (1988), and mitochondrial transit peptides such as those described in Boutry et al., *Nature* 328:340–342 (1987). Also included are sequences that result in localization of the encoded protein to various cellular compartments such as the vacuole. See, for example, Neuhaus et al., *Proc. Natl. Acad. Sci. USA* 88: 10362–10366 (1991) and Chrispeels, *Ann. Rev. Plant Physiol. Plant Mol. Biol.* 42: 21–53 (1991). The relevant disclosures of these publications are incorporated herein by reference in their entirety.

The chimeric DNA construct(s) of the invention may contain multiple copies of a promoter or multiple copies of the coding sequence for a biotin biosynthetic enzyme. In addition, the construct(s) may include coding sequences for markers and coding sequences for other peptides such as signal or transit peptides, each in proper reading frame with the other functional elements in the DNA molecule. The preparation of such constructs are within the ordinary level of skill in the art.

Useful markers include peptides providing herbicide, antibiotic or drug resistance, such as, for example, resistance to hygromycin, kanamycin, G418, gentamycin, lincomycin, methotrexate, glyphosate, phosphinothricin, or the like. These markers can be used to select cells transformed with the chimeric DNA constructs of the invention from untransformed cells. Other useful markers are peptidic enzymes that can be easily detected by a visible reaction, for example a color reaction, for example luciferase, β-glucuronidase, or β-galactosidase.

Chimeric genes designed for plant expression such as those described herein can be introduced into the plant cell in a number of art-recognized ways. Those skilled in the art will appreciate that the choice of method might depend on the type of plant (i.e. monocot or dicot) and/or organelle (i.e. nucleus, chloroplast, mitochondria) targeted for transformation. Suitable methods of transforming plant cells include microinjection (Crossway et al., *BioTechniques* 4:320–334 (1986)), electroporation (Riggs et al, *Proc. Natl. Acad. Sci. USA* 83:5602–5606 (1986), Agrobacterium mediated transformation (Hinchee et al., Biotechnology 6:915–921 (1988)), direct gene transfer (Paszkowski et al., *EMBO J.* 3:2717–2722 (1984)), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., *Biotechnology* 6:923–926 (1988)).see also, Weissinger et al., *Annual Rev. Genet.* 22:421–477 (1988); Sanford et al., *Particulate Science and Technology* 5:27–37 (1987)(onion); Christou et al., *Plant Physiol.* 87:671–674 (1988)(soybean); McCabe et al., *Bio/Technology* 6:923–926 (1988)(soybean); Datta et al., *Biotechnology* 8:736–740 (1990)(rice); Klein et al., *Proc. Natl. Acad. Sci. USA*, 85:4305–4309 (1988) (maize); Klein et al., *Bio/Technology* 6:559–563 (1988) (maize); Klein et al., *Plant Physiol.* 91:440–444 (1988) (maize); Fromm et al., *Bio/Technology* 8:833–839 (1990); and Gordon-Kamm et al., *Plant Cell* 2:603–618 (1990) (maize); Svab et al., *Proc. Natl. Acad. Sci. USA* 87:8526–8530 (1990)(tobacco chloroplasts); Gordon-Kamm et al, in "Transgenic Plants", vol. 2., pp.21–33, pub. by Academic Press (1993)(maize).

Once a chimeric gene encoding a biotin biosynthetic enzyme has been transformed into a particular plant species, it may be propagated in that species or moved into other varieties of the same species, particularly including commercial varieties, using traditional breeding techniques. Alternatively, the coding sequence for a biotin biosynthetic enzyme may be isolated, genetically engineered for optimal expression and then transformed into the desired variety.

The present invention is further directed to transgenic plant tissue, including plants, seeds, and cultured tissue, stably transformed with at least one chimeric gene capable of expressing a biotin biosynthetic enzyme in the plant tissue. Expression of such a chimeric gene results in an increase in the level of the encoded biotin biosynthetic enzyme Transgenic plant tissue of the invention contains enhanced levels of biotin resulting from the expression of the chimeric gene or chimeric genes contained therein that encode one or more biotin biosynthetic enzymes. The statement "enhanced levels of biotin" is intended to mean levels of biotin greater than that found in corresponding non-transgenic plant tissue that does not contain a chimeric gene capable of expressing a biotin biosynthetic enzyme in the plant tissue.

Representative plants of the invention include any plants that may be incorporated into an animal or human diet. Preferred are agronomically important animal or human food crops such as tobacco, soya, rape, sugar beet, maize, rice, wheat, barley, oats, rye, sorghum, millet, turf, forage and the like.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by Sambrook, et al., Molecular Cloning, eds., Cold Spring Harbor Laboratory Press, Cold Spring Harbor, N.Y. (1989) and by T. J. Silhavy, M. L. Berman, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Example 1

Enhanced Biotin Biosynthesis in Plants Transformed with a Chimeric Gene encoding a Biotin Biosynthetic Enzyme Generally, the *E. coli* bioA gene is expressed in tissues of the Arabidopsis biol auxotroph, which lacks the ability to make its own biotin (Patton et al., *Mol. Gen. Genet.* 251: 261–266 (1996), hereby incorporated by reference in its entirety). Previous biochemical evidence suggested that the biol mutant of Arabidopsis is defective in the DAP aminotransferase enzyme encoded by the bioA gene. Tissues from the resulting transgenic plants expressing the *E. coli* bioA gene not only grow in the absence of biotin, but surprisingly contain increased levels of biotin relative to non-transformed control plants. These results indicate that the level of biotin in plant tissues can be increased by expressing a chimeric gene that encodes a biotin biosynthetic enzyme. The specific details for this example are given below.

The bioA gene from *E. coli* strain K 12 (SEQ ID NO:3) is amplified with ApliTaq DNA polymerase using the standard PCR protocol (Perkin Elmer). The employed oligonucleotide primers are:
(forward) GGAATTCAGAAGACGAC ATGACAACGGACGATCTTGCCTTTGAC (SEQ ID NO:9) and
(reverse) GGAATTCAGGTACCAT TTATTGGCAAAAAAATGTTTCATCCTGTAC (SEQ ID NO:10) with the underlined nucleotides corresponding to the 5' and 3' ends of the bioA gene, respectively. The bases that are not underlined contain the EcoRI restriction recognition site GAATTC and a spacer of 8 or 10 nucleotides. The 1376 base pair product is ligated directly into the pCRII vector using the protocol and reagents provided in the TA cloning kit (Invitrogen; San Diego, Calif.). Plasmid DNA is prepared from cells containing the correct bioA insert using the Magic Miniprep kit (Promega; Madison Wis.), then sequenced by the chain termination method using dideoxy terminators labeled with fluorescent dyes (Applied Biosystems, Inc., Foster City, Calif.) to ensure the fidelity of the amplified and cloned product. Plasmid DNA containing the verified bioA sequence is digested with EcoRI (Promega; Madison, Wis.) to release the 1.3 kb bioA insert, then purified on 1% Sea Plaque agarose (FMC, Rockland, Me.). The EcoRI fragment is then ligated into the EcoRI site of pCGN1761, a plant expression cassette with the double 35S promoter (Kay et al., Science 236: 1299–1302 (1987)) and tml 3' terminator flanking the EcoRi site. This ligation mixture is transformed by electroporation (Life Technologies; Gaithersburg, Md.) into XL-1 Blue electrocompetant cells (Stratagene; LaJolla, Calif.).

Figure 1:
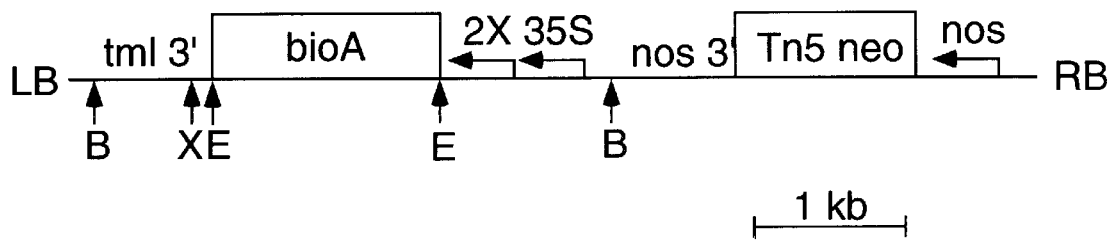
FIG. 1: T-DNA region of pCIB200/1761bioA

Plasmids containing the bioA gene in the correct orientation for expression are identified by standard restriction analysis (with BamHI). The expression unit containing the double 35S promoter, the bioA coding region, and the tml 3' termination sequence is cut out of the pCGN 1761 vector with XbaI, which recognizes restriction sites that occur just outside of the desired region. The 4.9 kb XbaI fragment is then ligated into the XbaI site in the T-DNA portion of the binary plasmid pCIB200. The resulting plasmid, pCIB200/1761bioA (see FIG. 1) is transferred to *Agrobacterium tumefaciens* strain c58 GV3101 (Bechtold et al. *C.R Acad. Sci. Paris, Sciences de la vie* 316: 1194–1199 (1993)) by electroporation using standard procedures. Agrobacterium cells containing the pCIB200/1761bioA binary vector are used to transform biotin-supplemented homozygous biol/biol Arabidopsis plants using the vacuum infiltration method (Bechtold et al., supra).

To select for stable transformants, seeds from the infiltrated plants are plated on biotin-free media containing Kanamycin. A kanamycin-resistant plant that grows in the absence of biotin (biol/A) is transferred to soil and assayed for total biotin production using the standard microbiological assay system (Scheiner, J. et al., *J. Agric. Food Chem.* 23: 1157–1162 (1975)) with dehydrated biotin assay medium (Difco; Detroit, Mich.). Leaf tissue from control Col-0 plants contains 18.1 pg total biotin per mg fresh weight, while leaves of the same age from the biollA plant produce 38.2 pg biotin per mg fresh weight. This represents a two-fold increase in total biotin produced in the mutant tissue expressing the *E. coli* bioA gene relative to non-transformed control plants. Additionally, kanamycin-resistant $T_2$ progeny from the biol/A plant contain elevated levels of biotin as expected.

Example 2

Isolation of additional biotin biosynthetic enzyme (BBE) genes based on sequence homology to known BBE coding sequences A phage or plasmid library is plated at a density of approximately 10,000 plaques on a 10 cm Petri dish, and filter lifts of the plaques are made after overnight growth of the plates at 37° C. The plaque lifts are probed with one of the cDNAs set forth in SEQ ID NOS:1, 3, 5, 7 and 11, labeled with 32P-dCTP by the random priming method by means of a PrimeTime kit (International Biotechnologies, Inc., New Haven, CT). Hybridization conditions are 7% sodium dodecyl sulfate (SDS), 0.5M NaPO4 pH 7.0, 1 mM EDTA at 50° C. After hybridization overnight, the filters are washed with 2×SSC, 1% SDS. Positively hybridizing plaques are detected by autoradiography. After purification to single plaques, cDNA inserts are isolated, and their sequences determined by the chain termination method using dideoxy terminators labeled with fluorescent dyes (Applied Biosystems, Inc., Foster City, Calif.).

The standard experimental protocol described above can be used by one of skill in the art to obtain BBE genes sequentially homologous to the known BBE coding sequences from any other eukaryote, particularly other higher plant species.

Example 3

Isolation of Plant Biotin Biosynthetic Genes Through Functional Complementation of Bacterial Auxotrophic Mutants In general, auxotrophic mutants of *E. coli* that are deficient in one of the biotin biosynthetic enzymes are transformed with a library expressed plant genes (cDNA's). The plant genes are cloned en mass into a phagemid vector that can drive expression of plant cDNA's in bacteria. The transformed bacteria are then grown under selective conditions in the absence of biotin. Colonies that grow under these conditions should have the ability to synthesize their own biotin because the plant cDNA is providing the function that is missing in the original *E. coli* mutant.

Specifically, *E. coli* mutants are available for each step in the biotin biosynthetic pathway. These mutants are obtained from the *E. coli* Genetic Stock Center (New Haven, Conn.). The bacteria are rendered electrocompetent using standard techniques and frozen at −70° C. until transformation.

The general scheme for generating a plasmid library of expressed plant genes is to first construct a standard cDNA library in lambda phage, then perform an in vivo excision reaction on the entire library and plate at low density to obtain single colonies. The *E. coli* colonies are eluted off the surface of the plates, pelleted, then used to prepare plasmid DNA. In this case, each colony that grows following the excision reaction represents a single cDNA from the original phage-born library. An alternative strategy is to obtain a previously constructed cDNA library from either a DNA stock center (such as the Arabidopsis Stock Center, Columbus, Ohio), commercial sources (Stratagene, LaJolla, Calif.), or an academic colleague. Specific details for constructing a cDNA library in a suitable vector such as pBluescript are given in the package insert sent along with the kit (Stratagene, LaJolla, Calif.). This plasmid carries the IPTG-inducible lacZ promoter oriented to drive expression of the inserted plant cDNA's.

Approximately 100 ng of plasmid DNA isolated from the cDNA library is used to electroporate the competent *E. coli* mutant cells (thawed on ice) using standard settings (1.7 Kvolts per cm for 10 milliseconds at 200 OHMS resistance and 25 $\mu$FD capacitance) on a Gene-Pulser® electroporator (Bio-Rad Laboratories, Melville, N.Y.) and a cuvette with 0.1 cm electrode gap. The electroporated cells are resuspended in 1 mL SOC (Life Technologies, Gaithersburg, Md.) and incubated at 37° C. for 1 hour with vigorous agitation (200 rpm on a rotary shaker). The cells are pelleted in a clinical centrifuge at maximum speed for 5 minutes at room temperature. The cell pellet is resuspended in 5 mLs of Vogel-Bonner E-minimal media (Vogel, H. J. and D. M. Bonner, *J. Biol. Chem.* 218:97–106 (1956)) to wash away excess biotin. The pelleting and washing steps are repeated two more times with the final pellet being resuspended in 1 mL minimal media. Aliquots of 100 µL are spread onto 1.5% agar plates with minimal media containing ampicillin (to select for the plasmid), IPTG (to induce the promoter driving expression of the plant gene), and any nutrients, other than biotin, which the *E. coli* strain requires for growth (i.e. thiaminie). The plates are incubated at 37° C. for 2 to 3 days until colonies form. Plasmid DNA is isolated from 1 mL overnight cultures started by inoculating LB medium with single colonies picked with sterile toothpicks. Plasmids are retested for high-efficiency biotin complementation by retransforming the *E. coli* auxotroph as described. Inserts from plasmids that complement at high frequency are then sequenced and can be used as a probe on Southern and northern blots to verify copy number of the gene and to characterize expression patterns in the plant.

Example 4

Construction of Plant Transformation Vectors

Numerous transformation vectors are available for plant transformation, and genes encoding biotin biosynthetic enzymes can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptll gene, which confers resistance to kanamycin and related antibiotics (Messing & Vierra, *Gene* 19: 259–268 (1982); Bevan et al., *Nature* 304:184–187 (1983)), the bar gene, which confers resistance to the herbicide phosphinothricin (White et al., *Nucl Acids Res* 18: 1062 (1990), Spencer et al. Theor Appl Genet 79: 625–631(1990)), the hph gene, which confers resistance to the antibiotic hygromycin (Blochinger & Diggelmann, *Mol Cell Biol* 4: 2929–2931), and the dhfr gene, which confers resistance to methotrexate (Bourouis et al., *EMBO J.*2(7): 1099–1104 (1983)).

(1) Construction of Vectors Suitable for Agrobacterium Transformation

Many vectors are available for transforrnation using *Agrobacterium tumefaciens*. These typically carry at least one T-DNA border sequence and include vectors such as pBIN 19 (Bevan, *Nucl. Acids Res.* (1984)) and pXYZ. Below the construction of two typical vectors is described.

Construction of pCIB200 and pCIB2001

The binary vectors pCIB200 and pCIB2001 are used for the construction of recombinant vectors for use with Agrobacterium and are constructed in the following manner: pTJS75kan is created by NarI digestion of pTJS75 (Schmidhauser & Helinski, *J Bacteriol.* 164: 446–455 (1985)) allowing excision of the tetracycline-resistance gene, followed by insertion of an AccI fragment from pUC4K carrying an NPTII (Messing & Vierra, *Gene* 19: 259–268 (1982); Bevan et al., *Nature* 304: 184–187 (1983); McBride et aL, *Plant Molecular Biology* 14: 266–276 (1990)). XhoI linkers are ligated to the EcoRV fragment of pCIB7, which contains the left and right T-DNA borders, a plant selectable nos/nptll chimeric gene and the pUC polylinker (Rothstein et al., *Gene* 53: 153–161 (1987)), and the XhoI-digested fragment is cloned into SalI-digested pTJS75kan to create pCIB200 (see also example 19 of EP 0 332 104). pCIB200 contains the following unique polylinker restriction sites: EcoRI, SstI, KpnI, BglII, XbaI, and SalI. pCIB2001 is a derivative of pCIB200 that is created by the insertion into the polylinker of additional restriction sites. Unique restriction sites in the polylinker of pCIB2001 are EcoRI, SstI, KpnI, BglII, XbaI, SalI, Mlul, BclI, AvrII, ApaI, HpaI, and StuI. In addition to containing these unique restriction sites, pCIB2001 also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives thereof

The binary vector pCIB10 contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al., *Gene* 53: 153–161 (1987). Various derivatives of pCIB10 have been constructed that incorporate the gene for hygromycin B phosphotransferase described by Gritz et al., *Gene* 25: 179–188 (1983)). These derivatives enable selection of transgenic plant cells on hygromycin only (pCIB743), or hygromycin and kanamycin (pCIB715, pCIB717).

(2) Construction of Vectors Suitable for non-Agrobacterium Transformation.

Transformation without the use of *Agrobacterium tumefaciens* circumvents the requirement for T-DNA sequences in the chosen transformation vector and consequently vectors lacking these sequences can be utilized in addition to vectors such as the ones described above that contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and a 400 bp SmaI fragment containing the bar gene from *Streptomyces viridochromogenes* is excised and inserted into the HpaI site of pCIB3060 (Thompson et al. EMBO J 6: 2519–2523 (1987)). This generates pCIB3064, which comprises the bar gene under the control of the CaMV 35S promoter and terminator for herbicide selection, a gene for ampicillin resistance (for selection in *E. coli*), and a polylinker with the unique sites SphI, PstI, HindIII, and BamHI. This vector is suitable for the cloning of plant expression cassettes containing their own regulatory signals.

Construction of pSOG19 and pSOG35 pSOG35 is a transformation vector that utilizes the *E. coli* gene dihydrofolate reductase (DHFR) as a selectable marker conferring resistance to methotrexate. PCR is used to amplify the 35S promoter (~800 bp), intron 6 from the maize Adh 1 gene (~550 bp), and 18 bp of the GUS untranslated leader sequence from pSOG10. A 250 bp fragment encoding the *E. coli* dihydrofolate reductase type II gene is also amplified by PCR and these two PCR fragments are assembled with a SacI-PstI fragment from pBI221 (Clontech) that comprises the pUC19 vector backbone and the nopaline synthase terminator. Assembly of these fragments generated pSOG19, which contains the 35S promoter in fusion with the intron 6 sequence, the GUS leader, the DHFR gene, and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign sequences.

Example 5

Construction of Plant Expression Cassettes

Gene sequences intended for expression in transgenic plants are firstly assembled in expression cassettes behind a suitable promoter and upstream of a suitable transcription terminator. These expression cassettes can then be easily transferred to the plant transformation vectors described above in Example 4.

Promoter Selection

The selection of a promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and this selection will reflect the desired location of expression of the transgene. Alternatively, the selected promoter may drive expression of the gene under a light-induced or other temporally regulated promoter. A further alternative is that the selected promoter be chemically regulated. This would provide the possibility of inducing expression of the transgene only when desired and caused by treatment with a chemical inducer.

Transcriptional Terminators

A variety of transcriptional terminators are available for use in expression cassettes. These are responsible for the termination of transcription beyond the transgene and its correct polyadenylation. Appropriate transcriptional terminators and those that are known to function in plants and include the CaMV 35S terminator, the tml terminator, the nopaline synthase terminator, the pea rbcS E9 terminator. These can be used in both monocotyledons and dicotyledons.

Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 is particularly effective and enhances expression in fusion constructs with the chloramphenicol acetyltransferase gene (Callis et al., *Genes Develop.* 1: 1183–1200 (1987)). In the same experimental system, the intron from the maize bronze1 gene has a similar effect in enhancing expression (Callis et al., supra). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al. *Plant Molec. Biol.* 15: 65–79 (1990))

Targeting of the Gene Product Within the Cell

Various mechanisms for targeting gene products are known to exist in plants and the sequences controlling the functioning of these mechanisms have been characterized in some detail. These mechanisms generally utilize identified transit peptides or internal amino acid sequences that have been found to target associated proteins to various cellular compartments such as the chloroplast, the mitochondrion, the peroxisome, the nucleus, the ER, the apoplast, and the vacuole.

Chloroplast Targeting

The targeting of gene products to the chloroplast is controlled by a signal sequence found at the amino terminal end of various proteins, which is cleaved during chloroplast import yielding the mature protein (e.g. Comai et al., *J. Biol. Chem.* 263: 15104–15109 (1988)). These signal sequences can be fused to heterologous gene products to effect the import of heterologous products into the chloroplast (van den Broeck et al. *Nature* 313: 358–363 (1985)). DNA encoding for appropriate signal sequences can be isolated from the 5' end of the cDNAs encoding the RUBISCO protein, the CAB protein, the EPSP synthase enzyme, the GS2 protein, and many other proteins that are known to be chloroplast localized.

Chen & Jagendorf (*J. Biol. Chem.* 268: 2363–2367 (1993)) have described the successful use of a chloroplast transit peptide for import of a heterologous transgene. This peptide used is the transit peptide from the rbcS gene from *Nicotiana plumbaginifolia* (Poulsen et al. *Mol. Gen. Genet.* 205: 193–200 (1986)). Using the restriction enzymes DraI and SphI, or Tsp509I and SphI the DNA sequence encoding this transit peptide can be excised from plasmid prbcS-8B (Poulsen et al. supra) and manipulated for use with any of the constructions described above. The DraI-SphI fragment extends from −58 relative to the initiating rbcS ATG to, and including, the first amino acid (also a methionine) of the mature peptide immediately after the import cleavage site, whereas the Tsp509I-SphI fragment extends from −8 relative to the initiating rbcS ATG to, and including, the first amino acid of the mature peptide. Thus, these fragment can be appropriately inserted into the polylinker of any chosen expression cassette generating a transcriptional fusion to the untranslated leader of the chosen promoter (e.g. 35S, PR-1a, actin, ubiquitin etc.), whilst enabling the insertion of a BBE gene in correct fusion downstream of the transit peptide. Constructions of this kind are routine in the art. For example, whereas the DraI end is already blunt, the 5' Tsp509I site may be rendered blunt by T4 polymerase treatment, or may alternatively be ligated to a linker or adaptor sequence to facilitate its fusion to the chosen promoter. The 3' SphI site may be maintained as such, or may alternatively be ligated to adaptor of linker sequences to facilitate its insertion into the chosen vector in such a way as to make available appropriate restriction sites for the subsequent insertion of a selected APS gene. Ideally the ATG of the SphI site is maintained and comprises the first ATG of the selected APS gene. Chen & Jagendorf (supra) provide consensus sequences for ideal cleavage for chloroplast import, and in each case a methionine is preferred at the first position of the mature protein. At subsequent positions there is more variation and the amino acid may not be so critical. In any case, fusion constructions can be assessed for efficiency of import in vitro using the methods described by Bartlett et al. (In: Edelmann et al. (Eds.) Methods in Chloroplast Molecular Biology, Elsevier. pp 1081–1091 (1982)) and Wasmann et al. (*Mol. Gen. Genet.* 205: 446–453 (1986)). Typically the best approach may be to generate fusions using the selected BBE gene with no modifications at the aminoterminus, and only to incorporate modifications when it is apparent that such fusions are not chloroplast imported at high efficiency, in which case modifications may be made in accordance with the established literature (Chen & Jagendorf, supra; Wasman et al., supra; Ko & Ko, *J. Biol. Chem.* 267: 13910–13916 (1992)).

Targeting to Other Plant Cellular Compartments

Other gene products are localized to organelles such as the mitochondrion and the peroxisome (e.g. Unger et al. *Plant Molec. Biol.* 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al., *Proc. Natl. Acad. Sci. USA* 82: 6512–6516 (1985)).

In addition, sequences have been characterized that cause the targeting of gene products to other cell compartments. Amino terminal sequences are responsible for targeting to the ER, the apoplast, and extracellular secretion from aleurone cells (Koehler & Ho, *Plant Cell* 2: 769–783 (1990)). Additionally, amino terminal sequences in conjunction with carboxy-terminal sequences are responsible for vacuolar targeting of gene products (Shinshi etal., *Plant Molec. Biol.* 14: 357–368 (1990)).

Transgene Targeting

By the fusion of the appropriate targeting sequences described above to transgene sequences of interest it is possible to direct the transgene product to any organelle or cell compartment. For chloroplast targeting, for example, the chloroplast signal sequence from the Arabidopsis BioB gene (see Example 8), the RUBISCO gene, the CAB gene, the EPSP synthase gene, or the GS2 gene is fused in frame to the amino terminal ATG of the transgene. The signal sequence selected should include the known cleavage site and the fusion constructed should take into account any amino acids after the cleavage site that are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) *Methods in Chloroplast Molecular Biology*, Elsevier. pp 1081–1091 (1982); Wasmann et al. *Mol. Gen. Genet.* 205: 446–453 (1986)). These construction techniques are well known in the art and are equally applicable to mitochondria and peroxisomes. The choice of targeting that may be required for expression of the transgenes will depend on the cellular localization of the precursor required as the starting point for a given pathway. This will usually be cytosolic or chloroplastic, although it may is some cases be mitochondrial or peroxisomal. The products of transgene expression will not normally require targeting to the ER, the apoplast or the vacuole.

The above described mechanisms for cellular targeting can be utilized not only in conjunction with their cognate promoters, but also in conjunction with heterologous promoters so as to effect a specific cell targeting goal under the transcriptional regulation of a promoter that has an expression pattern different to that of the promoter from which the targeting signal derives.

Example 6

Transformation of Dicotyledons

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., *EMBO J* 3: 2717–2722 (1984), Potrykus et al., *Mol. Gen. Genet.* 199: 169–177 (1985), Reich et al., *Biotechnology* 4: 1001–1004 (1986), and Klein et al., *Nature* 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species that are routinely transformable by Agrobacterium include tobacco, tomato, sunflower, cotton, oilseed rape, potato, soybean, alfalfa and poplar (EP 0 317 51 1 (cotton), EP 0 249 432 (tomato, to Calgene), WO 87/07299 (Brassica, to Calgene), U.S. Pat. No. 4,795,855 (poplar)). Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. *Plant Cell* 5: 159–169 (1993)). The transfer of the recombinant binary vector to Agrobacterium is accomplished by a triparental mating procedure using *E. coli* carrying the recombinant binary vector, a helper *E. coli* strain that carries a plasmid such as pRK2013 and that is able to mobilize the recombinant binary vector to the target Agrobacterium strain. Alternatively, the recombinant binary vector can be transferred to Agrobacterium by DNA transformation (Höfgen & Willmitzer, *Nucl. Acids Res.* 16: 9877(1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Example 7

Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4: 1093–1096 (1986)).

Patent Applications EP 0 292 435 (to Ciba-Geigy), EP 0 392 225 (to Ciba-Geigy) and WO 93/07278 (to Ciba-Geigy) describe techniques for the preparation of callus and protoplasts from an élite inbred line of maize, transformation of protoplasts using PEG or electroporation, and the regeneration of maize plants from transformed protoplasts. GordonKamm et al., *Plant Cell* 2: 603–618 (1990)) and Fromm et al., *Biotechnology* 8: 833–839 (1990)) have published techniques for transformation of A188-derived maize line using particle bombardment. Furthermore, application WO 93/07278 (to Ciba-Geigy) and Koziel et al., *Biotechnology* 11: 194–200 (1993)) describe techniques for the transformation of élite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., *Plant Cell Rep* 7: 379–384 (1988); Shimamoto et al. *Nature* 338: 274–277 (1989); Datta et al. *Biotechnology* 8: 736–740 (1990)). Both types are also routinely transformable using particle bombardment (Christou et al. *Biotechnology* 9: 957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation has been described by Vasil et al., *Biotechnology* 10: 667–674 (1992)) using particle bombardment into cells of type C long-term regenerable callus, and also by Vasil et al., *Biotechnology* 11: 1553–1558 (1993)) and Weeks et al., *Plant Physiol.* 102: 1077–1084 (1993) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashige & Skoog, *Physiologia Plantarum* 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics' helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS +1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" that contained half-strength MS, 2% sucrose, and the same concentration of selection agent. Patent application 08/147,161 describes methods for wheat transformation and is hereby incorporated by reference.

Example 8

Isolation of an Arabidopsis Biotin Biosynthetic Gene (BioB Homologue) Based on Sequence Homology to an Expressed Sequence Tag (EST)

This example describes the isolation of a full length cDNA clone from Arabidopsis that encodes the homologue of the BioB protein from bacteria and yeast. See also, Patton et al., *Plant Physiol.* 112: 371–378 (1996), hereby incorporated by reference in its entirety. The BioB protein plays an enzymatic role in the conversion of desthiobiotin to biotin, which involves the formation of the intermediate 9-mercaptodesthiobiotin.

The EST Database

The method used to isolate this clone is based upon homology to an EST (expressed sequence tag). An EST is a randomly isolated and partially sequenced cDNA clone of an expressed gene derived from a pool of mRNA isolated from an organism Since an EST is generated at random from an mRNA population and with only limited sequence information available, it cannot typically be associated with a particular function or activity based upon its mode of isolation. However, an EST may be associated with a particular function or activity based on sequence homology to genes with known function.

To date, over 14,000 EST clones from Arabidopsis have been generated and sequenced. These clones represent a portion of the total number of expressed Arabidopsis genes. For each EST approximately 300 base pairs of gene sequence from each end of these clones has been translated in all 6 possible reading frames and compared by BLAST homology searches (S. F. Altschul, et. al., *J. Mol. Biol.* 215: 403–410 (1990)) to all known protein sequences in the Genbank database. Periodically a list of the EST clones that have been generated is published in an electronic database called AATDB (an Arabidopsis thaliana data base), which includes identifying information for the EST (clone name, Genbank accession #, DNA sequence) and a list of protein sequences identified from the aforementioned BLAST search that have the strongest homology to the translated EST sequence. A stock of these clones are maintained in *E. coli* at Ohio State University (Columbus, Ohio) for public distribution.

Isolation of the Full Length BioB Homologue from Arabidopsis

An EST clone designated 86E12 (genbank accession #T20529) has homology to the *E. coli* BioB protein in the AATDB. This partial cDNA clone is obtained from the Arabidopsis stock center at Ohio State University center and confirmed by sequence analysis to be the same as listed as 86E12 in the AATDB. The 800 base pair insert from 86E12 is isolated and purified using standard molecular biology techniques. Using this insert as a probe, a 1.1 kb transcript is detected on a northern blot of RNA isolated from Arabidopsis leaves, indicating that 86E12 is not a full length clone. A single band is detected on Southern blots of total Arabidopsis DNA using the 86E12 insert as a probe, suggesting that the gene in the Arabidopsis genome corresponding to 86E12 is a single copy.

The 800 bp insert fragment from 86E12 is then used as a probe to isolate a full length clone from an Arabidopsis cDNA library. Approximately 250,000 plaques are screened using the labelled 800 bp insert from 86E12. Three clones that hybridized to the labelled insert are purified to homogeneity and compared by standard restriction analysis. All three clones are similar in composition except that one clone is missing the Xho I cloning site at the 3' terminus. The two remaining clones appear to be identical, one of which (pMAP101) is sequenced completely. pMAP101 was deposited as an *E. coli* cell stock on Feb. 6, 1995 in the Agricultural Research Service Culture Collection (NRRL #B-21398) in Peoria, Ill. The DNA sequence of the insert from this clone is set forth in SEQ ID No: 13. The amino acid sequence of the protein encoded by this cDNA is set forth in SEQ ID No: 14.

A comparison of the deduced protein sequence encoded by this gene and the *E. coli* BioB protein reveals over 50% identity and over 60% homology over the entire length of the two polypeptides (see FIG. 2). Considering the evolutionary divergence between plants and bacteria, this level of homology is remarkable and is compelling evidence that the cloned plant cDNA encodes a protein that is the functional homologue of the *E. coli* BioB protein.

Another interesting feature of this comparison is the number of excess amino acid residues on the amino terminus of the plant BioB homologue. This stretch of excess amino acids has characteristics typical of chloroplast transit peptides, indicating that this protein and other enzymes in the biotin biosynthetic pathway may be located and active in the chloroplast in plants. Thus, in order to express this gene and other BBE encoding genes in a plant to achieve enhanced biotin synthesis according to the invention, expression may be directed to the chloroplasts. This would not require any modification to BBE encoding genes such as the Arabidopsis gene described in this example, which naturally contain a chloroplast transit peptide coding sequence. For BBE encoding genes that do not naturally contain a chloroplast transit peptide coding sequence such as the bacterial BBE encoding gene, a chloroplast transit peptide encoding sequence as described in Example 5 (see "Chloroplast Targeting section) can be added to target the BBE to the chloroplast.

Example 9

Expression of the *E. coli* bioB gene behind the Arabidopsis 2S-2 promoter in Arabidopsis results in increased total biotin in siliques (seeds)

To achieve high level expression of the *E. coli* bioB gene in Arabidopsis seeds a chimeric gene construct is made by PCR-mediated ligation as described below. This construct contains the Arabidopsis 2S-2 seed-specific albumin promoter (Guerche et al., 1990) driving expression of the *E. coli* bioB gene (SEQ ID NO:7), followed by a polyadenylation signal sequence from the 35S terminator. Plants transformed with this construct are allowed to self-pollinate and the resulting seeds are assayed for total biotin.

First, the 1364 base pair 2S-2 promoter is amplified using standard PCR conditions with 100 ng of Arabidopsis Col-0 DNA and the primer pair DP199 and DP200 shown below:

DP199 (forward) 5'-GATC GAATTCGCTGCTCTCTAAAAAGTCAT G-3' (SEQ ID NO:15) and

DP200 (reverse) 5'-CTCGAGATCGTACG CCATGGTTTTGCTATTTGTGTTTGTATTC -3' (SEQ ID NO:16).

The underlined region in DP199 adds an EcoRI restriction recognition site to the 5' end of the promoter and the underlined regions in DP 200 add NcoI and XhoI sites to the 3' end of the promoter for directional cloning of inserts.

Second, the 78 base pair 35S terminator region is amplified from plasmid pCIB5521 using primer DP201 and DP202 shown below:

DP201 (forward) 5'-CCATTGCGTACGAT CTCGAGACTTAGTATGTATTTGTATTTG -3' (SEQ ID NO:17) and DP202 (reverse) 5'-GATCGGTACC GAATTCGTACCCACTGGATTTTGG -3' (SEQ ID NO:18).

Primer DP200 adds NcoI and XhoI sites to the 5' of this second product and DP202 adds an EcoRI site to the 3' end. Primers DP200 and DP201 have 20 bases of homology such that the products from the two above reactions can anneal over this stretch and serve as a template to amplify the desired final product.

This third PCR reaction is performed on products from the first two reactions using primers DP199 and DP202. The product of this amplification reaction is cut with EcoRI then ligated into general cloning vector pBluescriptII SK+ creating plasmid pDP205. The EcoRI insert is then sequenced to verify nucleic acid content. The EcoRI insert from pDP205 is then ligated into pUC19 to create pDP205a, which is then used to construct the final chimeric gene with the inserted bioB gene from *E. coli*.

Restriction recognition sites for NcoI and XhoI are added to the 5' and 3' ends of the coding region for the *E. coli* bioB gene (bases 2012 to 3052 of GenBank Accession J04423 -SEQ ID NO:7) using PCR amplification with primers DP205 and DP206 shown below:

DP205 (forward) 5'-GTCA CCATGGCTCACCGCCCACGC-3' (SEQ ID NO:19) and

DP206 (reverse) 5'-GGAT CTCGAGTCATAATGCTGCCGCGTTG-3' (SEQ ID NO:20).

Primer DP205 add an NcoI restriction recognition site at the ATG "start codon" of the bioB gene and DP206 adds an XhoI site just after the TGA "stop codon" for cloning into the 2S-2 expression cassette pDP205 creating plasmid pDP211.

The final chimeric gene in pDP211 including the 2S-2 promoter driving the *E. coli* bioB gene and terminated by the 35S terminator is cut out of pDP205 as an EcoRI fragment and ligated into the EcoRI site of the Agrobacterium binary vector pCIB200 creating plasmid pKN102. The new binary containing the chimeric bioB gene is transformed into Agrobacterium strain GV3101 (pMP90) using electroporation. Agrobacterium cultures containing the new plasmid are used to transform Arabidopsis by the vacuum infiltration method. T1 seeds are harvested and plated on kanamycin to select for primary (T1) transformants. Kanamycin resistant T1 seedlings are transferred to soil and grown to maturity. Three to five mature green siliques are harvested from each T1 plant and assayed for total biotin. FIG. 3 shows the unexpected result that many transgenic lines contain significantly more biotin than untransformed controls.

Example 10

Overexpression of the Arabidopsis biotin synthase in Arabidopsis behind the 35S promoter results in enhanced biotin accumulation A chimeric gene construct is made that contains the Arabidopsis biotin synthase coding region (SEQ ID NO:13) from the BIO2 gene and whose expression is driven by the double 35S promoter. The BIO2 cDNA is cut out of pMP101 with EcoRI and XhoI and ligated into the expression cassette region of pCGN1761. The resulting plasmid contains the appropriate expression cassette flanked by XbaI restriction recognition sites. The expression cassette is cut out with XbaI and ligated into the XbaI site of the binary plasmid pCIB200 resulting in new plasmid pMP102.

Plasmid pMP102 is then transformed into Agrobacterium strain GV3101 pMP90 by electroporation. Cultures of Agrobacterium cells harboring pMP102 are used to transform Arabidopsis Col-0 by vacuum infiltration. Seeds from infiltrated plants are surface sterilized and germinated on standard MS medium supplemented with kanamycin. Antibiotic resistant primary (T1) transformants are transplanted to soil and grown to maturity in a growth chamber under standard conditions (20+/−3C; 16 h light/8 h dark cycles).

T2 seeds from selfed T1 plants are selected on kanamycin as described. Kanamycin resistant T2 seedlings are transferred to soil and grown as described above. Mature leaves from four or five four week old T2 plants from each T1 line are assayed for total biotin using the Lactobacillus bioassay system (Shellhammer 1991) and compared to untransformed controls (see FIG. 4). Several T1 lines produce progeny T2 plants with unexpectedly increased total biotin levels (lines 1, 4, 8, 10, 11, 12, 14, and 15).

Various modifications of the invention described herein will become apparent to those skilled in the art. Such modifications are intended to fall within the scope of the appended claims.

---

What is claimed is:

1. A transgenic plant, plant cell, or plant issue that produces enhanced levels of biotin relative to the amount of biotin naturally in a non-transgenic plant, plant cell, or plant tissue, comprising a chimeric gene encoding a biotin biosynthetic enzyine that is expressed at elevated levels in said transgenic plant, plant cell, or plant tissue, wherein said biotin biosynthetic enzyme is selected from the group consisting of DAP aminotransferase and biotin synthase.

2. The transgenic plant or plant tissue of claim 1, wherein said biotin biosynthetic enzyme is a DAP aminotransferase.

3. The transgenic plant or plant tissue of claim 1, wherein said biotin biosynthetic enzyme is a biotin synthase.

4. The transgenic plant or plant tissue of claim 1, wherein said plant is selected from the group consisting of Arabidopsis, wheat, corn, soybean, canola, tobacco.

5. The transgenic plant or plant tissue of claim 1, wherein said chimeric gene comprises a chloroplast transit peptide signal sequence.

6. The transgenic plant or plant tissue of claim 1, wherein said biotin biosynthetic enzyme naturally occurs in a bacteria.

7. The transgenic plant or plant tissue of claim 1, wherein said biotin biosynthetic enzyme naturally occurs in a plant.

8. A method for increasing the amount of biotin in a plant, plant cell, or plant tissue relative to the amount of biotin naturally in said plant, plant cell, or plant tissue, comprising transforming said plant, plant cell, or plant tissue with a chimeric gene comprising a coding region that encodes a biotin biosynthetic enzyme selected from the group consisting of DAP aminotransferase and biotin synthase, whereby said biotin biosynthetic enzyme is expressed at elevated levels in said plant, plant cell, or plant tissue.

9. The method of claim 8, wherein said biotin biosynthetic enzyme is a DAP aminotransferase.

10. The method of claim 8, wherein said biotin biosynthetic enzyme is a biotin synthase.

11. The method of claim 8, wherein said chimeric gene comprises a chloroplast transit peptide signal sequence.

12. The method of claim 8, wherein said biotin biosynthetic enzyme naturally occurs in a bacteria.

13. The method of claim 8, wherein said biotin biosynthetic enzyme naturally occurs in a plant.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 1155 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 1..1152
        ( C ) IDENTIFICATION METHOD: experimental
        ( D ) OTHER INFORMATION: /product="KAP synthetase"
            / evidence= EXPERIMENTAL ( x i ) SEQUENCE DESCRIPTION: SEQ ID NO:1:

```
ATG  AGC  TGG  CAG  GAG  AAA  ATC  AAC  GCG  GCG  CTC  GAT  GCG  CGG  CGT  GCT       48
Met  Ser  Trp  Gln  Glu  Lys  Ile  Asn  Ala  Ala  Leu  Asp  Ala  Arg  Arg  Ala
 1             5                        10                       15

GCC  GAT  GCC  CTG  CGT  CGC  CGT  TAT  CCG  GTG  GCG  CAA  GGA  GCC  GGA  CGC       96
Ala  Asp  Ala  Leu  Arg  Arg  Arg  Tyr  Pro  Val  Ala  Gln  Gly  Ala  Gly  Arg
                     20                       25                   30

TGG  CTG  GTG  GCG  GAT  GAT  CGC  CAG  TAT  CTG  AAC  TTT  TCC  AGT  AAC  GAT      144
Trp  Leu  Val  Ala  Asp  Asp  Arg  Gln  Tyr  Leu  Asn  Phe  Ser  Ser  Asn  Asp
                35                       40                   45

TAT  TTA  GGT  TTA  AGC  CAT  CAT  CCG  CAA  ATT  ATC  CGT  GCC  TGG  CAG  CAG      192
```

| | | | | | | | | | | | | | | | | |
|---|---|---|---|---|---|---|---|---|---|---|---|---|---|---|---|---|
| Tyr | Leu | Gly | Leu | Ser | His | His | Pro | Gln | Ile | Ile | Arg | Ala | Trp | Gln | Gln | |
| | 50 | | | | | 55 | | | | | 60 | | | | | |

| GGG | GCG | GAG | CAA | TTT | GGC | ATC | GGT | AGC | GGC | GGC | TCC | GGT | CAC | GTC | AGC | 240 |
|---|---|---|---|---|---|---|---|---|---|---|---|---|---|---|---|---|
| Gly | Ala | Glu | Gln | Phe | Gly | Ile | Gly | Ser | Gly | Gly | Ser | Gly | His | Val | Ser | |
| 65 | | | | 70 | | | | | 75 | | | | | | 80 | |

| GGT | TAT | AGC | GTG | GTG | CAT | CAG | GCA | CTG | GAA | GAA | GAG | CTG | GCC | GAG | TGG | 288 |
|---|---|---|---|---|---|---|---|---|---|---|---|---|---|---|---|---|
| Gly | Tyr | Ser | Val | Val | His | Gln | Ala | Leu | Glu | Glu | Glu | Leu | Ala | Glu | Trp | |
| | | | | 85 | | | | | 90 | | | | | 95 | | |

| CTT | GGC | TAT | TCG | CGG | GCA | CTG | CTG | TTT | ATC | TCT | GGT | TTC | GCC | GCT | AAT | 336 |
|---|---|---|---|---|---|---|---|---|---|---|---|---|---|---|---|---|
| Leu | Gly | Tyr | Ser | Arg | Ala | Leu | Leu | Phe | Ile | Ser | Gly | Phe | Ala | Ala | Asn | |
| | | | 100 | | | | | 105 | | | | | 110 | | | |

| CAG | GCA | GTT | ATT | GCC | GCG | ATG | ATG | GCG | AAA | GAG | GAC | CGT | ATT | GCT | GCC | 384 |
|---|---|---|---|---|---|---|---|---|---|---|---|---|---|---|---|---|
| Gln | Ala | Val | Ile | Ala | Ala | Met | Met | Ala | Lys | Glu | Asp | Arg | Ile | Ala | Ala | |
| | | 115 | | | | | 120 | | | | | 125 | | | | |

| GAC | CGG | CTT | AGC | CAT | GCC | TCA | TTG | CTG | GAA | GCT | GCC | AGT | TTA | AGC | CCG | 432 |
|---|---|---|---|---|---|---|---|---|---|---|---|---|---|---|---|---|
| Asp | Arg | Leu | Ser | His | Ala | Ser | Leu | Leu | Glu | Ala | Ala | Ser | Leu | Ser | Pro | |
| | 130 | | | | | 135 | | | | | 140 | | | | | |

| TCG | CAG | CTT | CGC | CGT | TTT | GCT | CAT | AAC | GAT | GTC | ACT | CAT | TTG | GCG | CGA | 480 |
|---|---|---|---|---|---|---|---|---|---|---|---|---|---|---|---|---|
| Ser | Gln | Leu | Arg | Arg | Phe | Ala | His | Asn | Asp | Val | Thr | His | Leu | Ala | Arg | |
| 145 | | | | | 150 | | | | | 155 | | | | | 160 | |

| TTG | CTT | GCT | TCC | CCC | TGT | CCG | GGG | CAG | CAA | ATG | GTG | GTG | ACA | GAA | GGC | 528 |
|---|---|---|---|---|---|---|---|---|---|---|---|---|---|---|---|---|
| Leu | Leu | Ala | Ser | Pro | Cys | Pro | Gly | Gln | Gln | Met | Val | Val | Thr | Glu | Gly | |
| | | | | 165 | | | | | 170 | | | | | | 175 | |

| GTG | TTC | AGC | ATG | GAC | GGC | GAT | AGT | GCG | CCA | CTG | GCG | GAA | ATC | CAG | CAG | 576 |
|---|---|---|---|---|---|---|---|---|---|---|---|---|---|---|---|---|
| Val | Phe | Ser | Met | Asp | Gly | Asp | Ser | Ala | Pro | Leu | Ala | Glu | Ile | Gln | Gln | |
| | | | 180 | | | | | 185 | | | | | 190 | | | |

| GTA | ACG | CAA | CAG | CAC | AAT | GGC | TGG | TTG | ATG | GTC | GAT | GAT | GCC | CAC | GGC | 624 |
|---|---|---|---|---|---|---|---|---|---|---|---|---|---|---|---|---|
| Val | Thr | Gln | Gln | His | Asn | Gly | Trp | Leu | Met | Val | Asp | Asp | Ala | His | Gly | |
| | | 195 | | | | | 200 | | | | | 205 | | | | |

| ACG | GGC | GTT | ATC | GGG | GAG | CAG | GGG | CGC | GGC | AGC | TGC | TGG | CTG | CAA | AAG | 672 |
|---|---|---|---|---|---|---|---|---|---|---|---|---|---|---|---|---|
| Thr | Gly | Val | Ile | Gly | Glu | Gln | Gly | Arg | Gly | Ser | Cys | Trp | Leu | Gln | Lys | |
| | 210 | | | | | 215 | | | | | 220 | | | | | |

| GTA | AAA | CCA | GAA | TTG | CTG | GTA | GTG | ACT | TTT | GGC | AAA | GGA | TTT | GGC | GTC | 720 |
|---|---|---|---|---|---|---|---|---|---|---|---|---|---|---|---|---|
| Val | Lys | Pro | Glu | Leu | Leu | Val | Val | Thr | Phe | Gly | Lys | Gly | Phe | Gly | Val | |
| 225 | | | | | 230 | | | | | 235 | | | | | 240 | |

| AGC | GGG | GCA | GCG | GTG | CTT | TGC | TCC | AGT | ACG | GTG | GCG | GAT | TAT | CTG | CTG | 768 |
|---|---|---|---|---|---|---|---|---|---|---|---|---|---|---|---|---|
| Ser | Gly | Ala | Ala | Val | Leu | Cys | Ser | Ser | Thr | Val | Ala | Asp | Tyr | Leu | Leu | |
| | | | | 245 | | | | | 250 | | | | | | 255 | |

| CAA | TTC | GCC | CGC | CAC | CTT | ATC | TAC | AGC | ACC | AGT | ATG | CCG | CCC | GCT | CAG | 816 |
|---|---|---|---|---|---|---|---|---|---|---|---|---|---|---|---|---|
| Gln | Phe | Ala | Arg | His | Leu | Ile | Tyr | Ser | Thr | Ser | Met | Pro | Pro | Ala | Gln | |
| | | | 260 | | | | | 265 | | | | | 270 | | | |

| GCG | CAG | GCA | TTA | CGT | GCG | TCG | CTG | GCG | GTC | ATT | CGC | AGT | GAT | GAG | GGT | 864 |
|---|---|---|---|---|---|---|---|---|---|---|---|---|---|---|---|---|
| Ala | Gln | Ala | Leu | Arg | Ala | Ser | Leu | Ala | Val | Ile | Arg | Ser | Asp | Glu | Gly | |
| | | 275 | | | | | 280 | | | | | 285 | | | | |

| GAT | GCA | CGG | CGC | GAA | AAA | CTG | GCG | GCA | CTC | ATT | ACG | CGT | TTT | CGT | GCC | 912 |
|---|---|---|---|---|---|---|---|---|---|---|---|---|---|---|---|---|
| Asp | Ala | Arg | Arg | Glu | Lys | Leu | Ala | Ala | Leu | Ile | Thr | Arg | Phe | Arg | Ala | |
| | 290 | | | | | 295 | | | | | 300 | | | | | |

| GGA | GTA | CAG | GAT | TTG | CCG | TTT | ACG | CTT | GCT | GAT | TCA | TGC | AGC | GCC | ATC | 960 |
|---|---|---|---|---|---|---|---|---|---|---|---|---|---|---|---|---|
| Gly | Val | Gln | Asp | Leu | Pro | Phe | Thr | Leu | Ala | Asp | Ser | Cys | Ser | Ala | Ile | |
| 305 | | | | | 310 | | | | | 315 | | | | | 320 | |

| CAG | CCA | TTG | ATT | GTC | GGT | GAT | AAC | AGC | CGT | GCG | TTA | CAA | CTG | GCA | GAA | 1008 |
|---|---|---|---|---|---|---|---|---|---|---|---|---|---|---|---|---|
| Gln | Pro | Leu | Ile | Val | Gly | Asp | Asn | Ser | Arg | Ala | Leu | Gln | Leu | Ala | Glu | |
| | | | | 325 | | | | | 330 | | | | | | 335 | |

| AAA | CTG | CGT | CAG | CAA | GGC | TGC | TGG | GTC | ACG | GCG | ATT | CGC | CCG | CCA | ACC | 1056 |
|---|---|---|---|---|---|---|---|---|---|---|---|---|---|---|---|---|
| Lys | Leu | Arg | Gln | Gln | Gly | Cys | Trp | Val | Thr | Ala | Ile | Arg | Pro | Pro | Thr | |
| | | | 340 | | | | | 345 | | | | | 350 | | | |

| GTA | CCC | GCT | GGT | ACT | GCG | CGA | CTG | CGC | TTA | ACG | CTA | ACC | GCT | GCG | CAT | 1104 |
|---|---|---|---|---|---|---|---|---|---|---|---|---|---|---|---|---|
| Val | Pro | Ala | Gly | Thr | Ala | Arg | Leu | Arg | Leu | Thr | Leu | Thr | Ala | Ala | His | |
| | | 355 | | | | | 360 | | | | | 365 | | | | |

| GAA | ATG | CAG | GAT | ATC | GAC | CGT | CTG | CTG | GAG | GTG | CTG | CAT | GGC | AAC | GGT | 1152 |

| Glu | Met | Gln | Asp | Ile | Asp | Arg | Leu | Leu | Glu | Val | Leu | His | Gly | Asn | Gly |
|---|---|---|---|---|---|---|---|---|---|---|---|---|---|---|---|
| | 370 | | | | 375 | | | | | 380 | | | | | |

TAA                                                                                                          1155

(2) INFORMATION FOR SEQ ID NO:2:

(i) SEQUENCE CHARACTERISTICS:
      (A) LENGTH: 384 amino acids
      (B) TYPE: amino acid
      (D) TOPOLOGY: linear (ii) MOLECULE TYPE: protein (xi) SEQUENCE DESCRIPTION: SEQ ID NO:2:

| Met | Ser | Trp | Gln | Glu | Lys | Ile | Asn | Ala | Ala | Leu | Asp | Ala | Arg | Arg | Ala |
|---|---|---|---|---|---|---|---|---|---|---|---|---|---|---|---|
| 1 | | | | 5 | | | | | 10 | | | | | 15 | |
| Ala | Asp | Ala | Leu | Arg | Arg | Arg | Tyr | Pro | Val | Ala | Gln | Gly | Ala | Gly | Arg |
| | | | 20 | | | | 25 | | | | | 30 | | | |
| Trp | Leu | Val | Ala | Asp | Asp | Arg | Gln | Tyr | Leu | Asn | Phe | Ser | Ser | Asn | Asp |
| | | 35 | | | | | 40 | | | | | 45 | | | |
| Tyr | Leu | Gly | Leu | Ser | His | His | Pro | Gln | Ile | Ile | Arg | Ala | Trp | Gln | Gln |
| | 50 | | | | | 55 | | | | | | 60 | | | |
| Gly | Ala | Glu | Gln | Phe | Gly | Ile | Gly | Ser | Gly | Gly | Ser | Gly | His | Val | Ser |
| 65 | | | | | 70 | | | | | 75 | | | | | 80 |
| Gly | Tyr | Ser | Val | Val | His | Gln | Ala | Leu | Glu | Glu | Glu | Leu | Ala | Glu | Trp |
| | | | | 85 | | | | | 90 | | | | | 95 | |
| Leu | Gly | Tyr | Ser | Arg | Ala | Leu | Leu | Phe | Ile | Ser | Gly | Phe | Ala | Ala | Asn |
| | | | 100 | | | | | 105 | | | | | 110 | | |
| Gln | Ala | Val | Ile | Ala | Ala | Met | Met | Ala | Lys | Glu | Asp | Arg | Ile | Ala | Ala |
| | | 115 | | | | | 120 | | | | | 125 | | | |
| Asp | Arg | Leu | Ser | His | Ala | Ser | Leu | Leu | Glu | Ala | Ala | Ser | Leu | Ser | Pro |
| | 130 | | | | | 135 | | | | | 140 | | | | |
| Ser | Gln | Leu | Arg | Arg | Phe | Ala | His | Asn | Asp | Val | Thr | His | Leu | Ala | Arg |
| 145 | | | | | 150 | | | | | 155 | | | | | 160 |
| Leu | Leu | Ala | Ser | Pro | Cys | Pro | Gly | Gln | Gln | Met | Val | Val | Thr | Glu | Gly |
| | | | | 165 | | | | | 170 | | | | | 175 | |
| Val | Phe | Ser | Met | Asp | Gly | Asp | Ser | Ala | Pro | Leu | Ala | Glu | Ile | Gln | Gln |
| | | | | 180 | | | | 185 | | | | | 190 | | |
| Val | Thr | Gln | Gln | His | Asn | Gly | Trp | Leu | Met | Val | Asp | Asp | Ala | His | Gly |
| | | | 195 | | | | 200 | | | | | 205 | | | |
| Thr | Gly | Val | Ile | Gly | Glu | Gln | Gly | Arg | Gly | Ser | Cys | Trp | Leu | Gln | Lys |
| | | 210 | | | | 215 | | | | | 220 | | | | |
| Val | Lys | Pro | Glu | Leu | Leu | Val | Val | Thr | Phe | Gly | Lys | Gly | Phe | Gly | Val |
| 225 | | | | | 230 | | | | | 235 | | | | | 240 |
| Ser | Gly | Ala | Ala | Val | Leu | Cys | Ser | Ser | Thr | Val | Ala | Asp | Tyr | Leu | Leu |
| | | | | 245 | | | | | 250 | | | | | 255 | |
| Gln | Phe | Ala | Arg | His | Leu | Ile | Tyr | Ser | Thr | Ser | Met | Pro | Pro | Ala | Gln |
| | | | 260 | | | | | 265 | | | | | 270 | | |
| Ala | Gln | Ala | Leu | Arg | Ala | Ser | Leu | Ala | Val | Ile | Arg | Ser | Asp | Glu | Gly |
| | | 275 | | | | | 280 | | | | | 285 | | | |
| Asp | Ala | Arg | Arg | Glu | Lys | Leu | Ala | Ala | Leu | Ile | Thr | Arg | Phe | Arg | Ala |
| | 290 | | | | | 295 | | | | | 300 | | | | |
| Gly | Val | Gln | Asp | Leu | Pro | Phe | Thr | Leu | Ala | Asp | Ser | Cys | Ser | Ala | Ile |
| 305 | | | | | 310 | | | | | 315 | | | | | 320 |
| Gln | Pro | Leu | Ile | Val | Gly | Asp | Asn | Ser | Arg | Ala | Leu | Gln | Leu | Ala | Glu |
| | | | | 325 | | | | | 330 | | | | | 335 | |

| Lys | Leu | Arg | Gln 340 | Gln | Gly | Cys | Trp | Val 345 | Thr | Ala | Ile | Arg | Pro 350 | Pro | Thr |
| Val | Pro | Ala 355 | Gly | Thr | Ala | Arg | Leu 360 | Arg | Leu | Thr | Leu | Thr 365 | Ala | Ala | His |
| Glu | Met 370 | Gln | Asp | Ile | Asp | Arg 375 | Leu | Leu | Glu | Val | Leu 380 | His | Gly | Asn | Gly |

( 2 ) INFORMATION FOR SEQ ID NO:3:

( i ) SEQUENCE CHARACTERISTICS:
        ( A ) LENGTH: 1296 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 1..1293
        ( C ) IDENTIFICATION METHOD: experimental
        ( D ) OTHER INFORMATION: /product="DAP aminotransferase"
                / evidence= EXPERIMENTAL ( x i ) SEQUENCE DESCRIPTION: SEQ ID NO:3:

| ATT | ATG | ACA | ACG | GAC | GAT | CTT | GCC | TTT | GAC | CAA | CGC | CAT | ATC | TGG | CAC | 48 |
| Ile | Met | Thr | Thr | Asp | Asp | Leu | Ala | Phe | Asp | Gln | Arg | His | Ile | Trp | His | |
| 385 | | | | | 390 | | | | | 395 | | | | | 400 | |

| CCA | TAC | ACA | TCC | ATG | ACC | TCC | CCT | CTG | CCG | GTT | TAT | CCG | GTG | GTG | AGC | 96 |
| Pro | Tyr | Thr | Ser | Met | Thr | Ser | Pro | Leu | Pro | Val | Tyr | Pro | Val | Val | Ser | |
| | | | | 405 | | | | | 410 | | | | | 415 | | |

| GCC | GAA | GGT | TGC | GAG | CTG | ATT | TTG | TCT | GAC | GGC | AGA | CGC | CTG | GTT | GAC | 144 |
| Ala | Glu | Gly | Cys | Glu | Leu | Ile | Leu | Ser | Asp | Gly | Arg | Arg | Leu | Val | Asp | |
| | | | 420 | | | | | 425 | | | | | 430 | | | |

| GGT | ATG | TCG | TCC | TGG | TGG | GCG | GCG | ATC | CAC | GGC | TAC | AAT | CAC | CCG | CAG | 192 |
| Gly | Met | Ser | Ser | Trp | Trp | Ala | Ala | Ile | His | Gly | Tyr | Asn | His | Pro | Gln | |
| | | | 435 | | | | | 440 | | | | | 445 | | | |

| CTT | AAT | GCG | GCG | ATG | AAG | TCG | CAA | ATT | GAT | GCC | ATG | TCG | CAT | GTG | ATG | 240 |
| Leu | Asn | Ala | Ala | Met | Lys | Ser | Gln | Ile | Asp | Ala | Met | Ser | His | Val | Met | |
| | | 450 | | | | | 455 | | | | | 460 | | | | |

| TTT | GGC | GGT | ATC | ACC | CAT | GCG | CCA | GCC | ATT | GAG | CTG | TGC | CGC | AAA | CTG | 288 |
| Phe | Gly | Gly | Ile | Thr | His | Ala | Pro | Ala | Ile | Glu | Leu | Cys | Arg | Lys | Leu | |
| 465 | | | | | 470 | | | | | 475 | | | | | 480 | |

| GTG | GCG | ATG | AGC | GGC | CGC | AAC | GCG | CTG | GAG | TGC | GTT | TTT | CTC | GCG | GAC | 336 |
| Val | Ala | Met | Ser | Gly | Arg | Asn | Ala | Leu | Glu | Cys | Val | Phe | Leu | Ala | Asp | |
| | | | | 485 | | | | | 490 | | | | | 495 | | |

| TCC | GGT | TCC | GTA | GCG | GTG | GAA | GTG | GCG | ATG | AAA | ATG | GCG | TTG | CAG | TAC | 384 |
| Ser | Gly | Ser | Val | Ala | Val | Glu | Val | Ala | Met | Lys | Met | Ala | Leu | Gln | Tyr | |
| | | | 500 | | | | | 505 | | | | | 510 | | | |

| TGG | CAA | GCC | AAA | GGC | GAA | GCG | CGC | CAG | CGT | TTT | CTG | ACC | TTC | CGC | AAT | 432 |
| Trp | Gln | Ala | Lys | Gly | Glu | Ala | Arg | Gln | Arg | Phe | Leu | Thr | Phe | Arg | Asn | |
| | | 515 | | | | | 520 | | | | | 525 | | | | |

| GGT | TAT | CAT | GGC | GAT | ACC | TTT | GGC | GCG | ATG | TCG | GTG | TGC | GAT | CCG | GAT | 480 |
| Gly | Tyr | His | Gly | Asp | Thr | Phe | Gly | Ala | Met | Ser | Val | Cys | Asp | Pro | Asp | |
| | | 530 | | | | | 535 | | | | | 540 | | | | |

| AAC | TCA | ATG | CAC | AGT | CTG | TGG | AAA | GGC | TAC | CTG | CCA | GAA | AAC | CTG | TTT | 528 |
| Asn | Ser | Met | His | Ser | Leu | Trp | Lys | Gly | Tyr | Leu | Pro | Glu | Asn | Leu | Phe | |
| 545 | | | | | 550 | | | | | 555 | | | | | 560 | |

| GCT | CCC | GCC | CCG | CAA | AGC | CGC | ATG | GAT | GGC | GAA | TGG | GAT | GAG | CGC | GAT | 576 |
| Ala | Pro | Ala | Pro | Gln | Ser | Arg | Met | Asp | Gly | Glu | Trp | Asp | Glu | Arg | Asp | |
| | | | | 565 | | | | | 570 | | | | | 575 | | |

| ATG | GTG | GGC | TTT | GCC | CGC | CTG | ATG | GCG | GCG | CAT | CGT | CAT | GAA | ATC | GCG | 624 |

```
Met  Val  Gly  Phe  Ala  Arg  Leu  Met  Ala  Ala  His  Arg  His  Glu  Ile  Ala
               580                      585                     590

GCG  GTG  ATC  ATT  GAG  CCG  ATT  GTC  CAG  GGC  GCA  GGC  GGG  ATG  CGC  ATG    672
Ala  Val  Ile  Ile  Glu  Pro  Ile  Val  Gln  Gly  Ala  Gly  Gly  Met  Arg  Met
          595                     600                     605

TAC  CAT  CCG  GAA  TGG  TTA  AAA  CGA  ATC  CGC  AAA  ATA  TGC  GAT  CGC  GAA    720
Tyr  His  Pro  Glu  Trp  Leu  Lys  Arg  Ile  Arg  Lys  Ile  Cys  Asp  Arg  Glu
     610                     615                     620

GGT  ATC  TTG  CTG  ATT  GCC  GAC  GAG  ATC  GCC  ACT  GGA  TTT  GGT  CGT  ACC    768
Gly  Ile  Leu  Leu  Ile  Ala  Asp  Glu  Ile  Ala  Thr  Gly  Phe  Gly  Arg  Thr
625                      630                     635                     640

GGG  AAA  CTG  TTT  GCC  TGT  GAA  CAT  GCA  GAA  ATC  GCG  CCG  GAC  ATT  TTG    816
Gly  Lys  Leu  Phe  Ala  Cys  Glu  His  Ala  Glu  Ile  Ala  Pro  Asp  Ile  Leu
                    645                     650                     655

TGC  CTC  GGT  AAA  GCC  TTA  ACC  GGC  GGC  ACA  ATG  ACC  CTT  TCC  GCC  ACA    864
Cys  Leu  Gly  Lys  Ala  Leu  Thr  Gly  Gly  Thr  Met  Thr  Leu  Ser  Ala  Thr
               660                     665                     670

CTC  ACC  ACG  CGC  GAG  GTT  GCA  GAA  ACC  ATC  AGT  AAC  GGT  GAA  GCC  GGT    912
Leu  Thr  Thr  Arg  Glu  Val  Ala  Glu  Thr  Ile  Ser  Asn  Gly  Glu  Ala  Gly
          675                     680                     685

TGC  TTT  ATG  CAT  GGG  CCA  ACT  TTT  ATG  GGC  AAT  CCG  CTG  GCC  TGC  GCG    960
Cys  Phe  Met  His  Gly  Pro  Thr  Phe  Met  Gly  Asn  Pro  Leu  Ala  Cys  Ala
     690                     695                     700

GCA  GCA  AAC  GCC  AGC  CTG  GCG  ATT  CTC  GAA  TCT  GGC  GAC  TGG  CAG  CAA   1008
Ala  Ala  Asn  Ala  Ser  Leu  Ala  Ile  Leu  Glu  Ser  Gly  Asp  Trp  Gln  Gln
705                     710                     715                     720

CAG  GTG  GCG  GAT  ATT  GAA  GTA  CAG  CTG  CGC  GAG  CAA  CTT  GCC  CCC  GCC   1056
Gln  Val  Ala  Asp  Ile  Glu  Val  Gln  Leu  Arg  Glu  Gln  Leu  Ala  Pro  Ala
                    725                     730                     735

CGT  GAT  GCC  GAA  ATG  GTT  GCC  GAT  GTG  CGC  GTA  CTG  GGG  GCC  ATT  GGC   1104
Arg  Asp  Ala  Glu  Met  Val  Ala  Asp  Val  Arg  Val  Leu  Gly  Ala  Ile  Gly
               740                     745                     750

GTG  GTC  GAA  ACC  ACT  CAT  CCG  GTG  AAT  ATG  GCG  GCG  CTG  CAA  AAA  TTC   1152
Val  Val  Glu  Thr  Thr  His  Pro  Val  Asn  Met  Ala  Ala  Leu  Gln  Lys  Phe
          755                     760                     765

TTT  GTC  GAA  CAG  GGT  GTC  TGG  ATC  CGG  CCT  TTT  GGC  AAA  CTG  ATT  TAC   1200
Phe  Val  Glu  Gln  Gly  Val  Trp  Ile  Arg  Pro  Phe  Gly  Lys  Leu  Ile  Tyr
     770                     775                     780

CTG  ATG  CCG  CCC  TAT  ATT  ATT  CTC  CCG  CAA  CAG  TTG  CAG  CGT  CTG  ACC   1248
Leu  Met  Pro  Pro  Tyr  Ile  Ile  Leu  Pro  Gln  Gln  Leu  Gln  Arg  Leu  Thr
785                     790                     795                     800

GCA  GCG  GTT  AAC  CGC  GCG  GTA  CAG  GAT  GAA  ACA  TTT  TTT  TGC  CAA        1293
Ala  Ala  Val  Asn  Arg  Ala  Val  Gln  Asp  Glu  Thr  Phe  Phe  Cys  Gln
                    805                     810                     815

TAA                                                                              1296
```

( 2 ) INFORMATION FOR SEQ ID NO:4:

( i ) SEQUENCE CHARACTERISTICS:
    ( A ) LENGTH: 431 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Ile  Met  Thr  Thr  Asp  Asp  Leu  Ala  Phe  Asp  Gln  Arg  His  Ile  Trp  His
1                   5                    10                      15

Pro  Tyr  Thr  Ser  Met  Thr  Ser  Pro  Leu  Pro  Val  Tyr  Pro  Val  Val  Ser
               20                      25                      30

Ala  Glu  Gly  Cys  Glu  Leu  Ile  Leu  Ser  Asp  Gly  Arg  Arg  Leu  Val  Asp
```

|     |     |     |     |     | 35  |     |     |     |     | 40  |     |     |     |     | 45  |
|-----|-----|-----|-----|-----|-----|-----|-----|-----|-----|-----|-----|-----|-----|-----|-----|

Gly Met Ser Ser Trp Trp Ala Ala Ile His Gly Tyr Asn His Pro Gln
     50                      55                      60

Leu Asn Ala Ala Met Lys Ser Gln Ile Asp Ala Met Ser His Val Met
 65                      70                      75                      80

Phe Gly Gly Ile Thr His Ala Pro Ala Ile Glu Leu Cys Arg Lys Leu
                     85                      90                      95

Val Ala Met Ser Gly Arg Asn Ala Leu Glu Cys Val Phe Leu Ala Asp
                100                     105                     110

Ser Gly Ser Val Ala Val Glu Val Ala Met Lys Met Ala Leu Gln Tyr
             115                     120                     125

Trp Gln Ala Lys Gly Glu Ala Arg Gln Arg Phe Leu Thr Phe Arg Asn
     130                     135                     140

Gly Tyr His Gly Asp Thr Phe Gly Ala Met Ser Val Cys Asp Pro Asp
145                     150                     155                     160

Asn Ser Met His Ser Leu Trp Lys Gly Tyr Leu Pro Glu Asn Leu Phe
                 165                     170                     175

Ala Pro Ala Pro Gln Ser Arg Met Asp Gly Glu Trp Asp Glu Arg Asp
             180                     185                     190

Met Val Gly Phe Ala Arg Leu Met Ala Ala His Arg His Glu Ile Ala
             195                     200                     205

Ala Val Ile Ile Glu Pro Ile Val Gln Gly Ala Gly Gly Met Arg Met
210                     215                     220

Tyr His Pro Glu Trp Leu Lys Arg Ile Arg Lys Ile Cys Asp Arg Glu
225                     230                     235                     240

Gly Ile Leu Leu Ile Ala Asp Glu Ile Ala Thr Gly Phe Gly Arg Thr
                 245                     250                     255

Gly Lys Leu Phe Ala Cys Glu His Ala Glu Ile Ala Pro Asp Ile Leu
             260                     265                     270

Cys Leu Gly Lys Ala Leu Thr Gly Gly Thr Met Thr Leu Ser Ala Thr
         275                     280                     285

Leu Thr Thr Arg Glu Val Ala Glu Thr Ile Ser Asn Gly Glu Ala Gly
290                     295                     300

Cys Phe Met His Gly Pro Thr Phe Met Gly Asn Pro Leu Ala Cys Ala
305                     310                     315                     320

Ala Ala Asn Ala Ser Leu Ala Ile Leu Glu Ser Gly Asp Trp Gln Gln
                 325                     330                     335

Gln Val Ala Asp Ile Glu Val Gln Leu Arg Glu Gln Leu Ala Pro Ala
             340                     345                     350

Arg Asp Ala Glu Met Val Ala Asp Val Arg Val Leu Gly Ala Ile Gly
         355                     360                     365

Val Val Glu Thr Thr His Pro Val Asn Met Ala Ala Leu Gln Lys Phe
370                     375                     380

Phe Val Glu Gln Gly Val Trp Ile Arg Pro Phe Gly Lys Leu Ile Tyr
385                     390                     395                     400

Leu Met Pro Pro Tyr Ile Ile Leu Pro Gln Gln Leu Gln Arg Leu Thr
                 405                     410                     415

Ala Ala Val Asn Arg Ala Val Gln Asp Glu Thr Phe Phe Cys Gln
             420                     425                     430

( 2 ) INFORMATION FOR SEQ ID NO:5:

( i ) SEQUENCE CHARACTERISTICS:
        ( A ) LENGTH: 660 base pairs
        ( B ) TYPE: nucleic acid ( C ) STRANDEDNESS: single
( D ) TOPOLOGY: linear ( i i ) MOLECULE TYPE: DNA (genomic)

( i i i ) HYPOTHETICAL: NO ( i x ) FEATURE:
( A ) NAME/KEY: CDS
( B ) LOCATION: 1..657
( C ) IDENTIFICATION METHOD: experimental
( D ) OTHER INFORMATION: /product="desthiobiotin
synthetase"
/ evidence= EXPERIMENTAL ( x i ) SEQUENCE DESCRIPTION: SEQ ID NO:5:

| GTG | AGT | AAA | CGT | TAT | TTT | GTC | ACC | GGA | ACG | GAT | ACC | GAA | GTG | GGG | AAA | 48 |
|---|---|---|---|---|---|---|---|---|---|---|---|---|---|---|---|---|
| Val | Ser | Lys | Arg | Tyr | Phe | Val | Thr | Gly | Thr | Asp | Thr | Glu | Val | Gly | Lys | |
| | | 435 | | | | | 440 | | | | | | 445 | | | |

| ACT | GTC | GCC | AGT | TGT | GCA | CTT | TTA | CAA | GCC | GCA | AAG | CGA | GCA | GGC | TAC | 96 |
| Thr | Val | Ala | Ser | Cys | Ala | Leu | Leu | Gln | Ala | Ala | Lys | Arg | Ala | Gly | Tyr | |
| | | 450 | | | | | 455 | | | | | 460 | | | | |

| CGG | ACG | GCA | GGT | TAT | AAA | CCG | GTC | GCC | TCT | GGC | AGC | GAA | AAG | ACC | CCG | 144 |
| Arg | Thr | Ala | Gly | Tyr | Lys | Pro | Val | Ala | Ser | Gly | Ser | Glu | Lys | Thr | Pro | |
| | 465 | | | | | 470 | | | | | 475 | | | | | |

| GAA | GGT | TTA | CGC | AAT | AGC | GAC | GCG | CTG | GCG | TTA | CAG | CGC | AAC | AGC | AGC | 192 |
| Glu | Gly | Leu | Arg | Asn | Ser | Asp | Ala | Leu | Ala | Leu | Gln | Arg | Asn | Ser | Ser | |
| 480 | | | | | 485 | | | | | 490 | | | | | 495 | |

| CTG | CAG | CTG | GAT | TAC | GCA | ACA | GTA | AAT | CCT | TAC | ACC | TTC | GCA | GAA | CCC | 240 |
| Leu | Gln | Leu | Asp | Tyr | Ala | Thr | Val | Asn | Pro | Tyr | Thr | Phe | Ala | Glu | Pro | |
| | | | | 500 | | | | | 505 | | | | | 510 | | |

| ACT | TCG | CCG | CAC | ATC | ATC | AGC | GCG | CAA | GAG | GGC | AGA | CCG | ATA | GAA | TCA | 288 |
| Thr | Ser | Pro | His | Ile | Ile | Ser | Ala | Gln | Glu | Gly | Arg | Pro | Ile | Glu | Ser | |
| | | | 515 | | | | | 520 | | | | | 525 | | | |

| TTG | GTA | ATG | AGC | GCC | GGA | TTA | CGC | GCG | CTT | GAA | CAA | CAG | GCT | GAC | TGG | 336 |
| Leu | Val | Met | Ser | Ala | Gly | Leu | Arg | Ala | Leu | Glu | Gln | Gln | Ala | Asp | Trp | |
| | | 530 | | | | | 535 | | | | | 540 | | | | |

| GTG | TTA | GTG | GAA | GGT | GCT | GGC | GGC | TGG | TTT | ACG | CCG | CTT | TCT | GAC | ACT | 384 |
| Val | Leu | Val | Glu | Gly | Ala | Gly | Gly | Trp | Phe | Thr | Pro | Leu | Ser | Asp | Thr | |
| | 545 | | | | | 550 | | | | | 555 | | | | | |

| TTC | ACT | TTT | GCA | GAT | TGG | GTA | ACA | CAG | GAA | CAA | CTG | CCG | GTG | ATA | CTG | 432 |
| Phe | Thr | Phe | Ala | Asp | Trp | Val | Thr | Gln | Glu | Gln | Leu | Pro | Val | Ile | Leu | |
| 560 | | | | | 565 | | | | | 570 | | | | | 575 | |

| GTA | GTT | GGT | GTG | AAA | CTC | GGC | TGT | ATT | AAT | CAC | GCG | ATG | TTG | ACT | GCA | 480 |
| Val | Val | Gly | Val | Lys | Leu | Gly | Cys | Ile | Asn | His | Ala | Met | Leu | Thr | Ala | |
| | | | | 580 | | | | | 585 | | | | | 590 | | |

| CAG | GTA | ATA | CAA | CAC | GCC | GGA | CTG | ACT | CTG | GCG | GGT | TGG | GTG | GCG | AAC | 528 |
| Gln | Val | Ile | Gln | His | Ala | Gly | Leu | Thr | Leu | Ala | Gly | Trp | Val | Ala | Asn | |
| | | | 595 | | | | | 600 | | | | | 605 | | | |

| GAT | GTT | ACG | CCT | CCG | GGA | AAA | CGT | CAC | GCT | GAA | TAT | ATG | ACC | ACG | CTC | 576 |
| Asp | Val | Thr | Pro | Pro | Gly | Lys | Arg | His | Ala | Glu | Tyr | Met | Thr | Thr | Leu | |
| | | 610 | | | | | 615 | | | | | 620 | | | | |

| ACC | CGC | ATG | ATT | CCG | CGC | CGC | TGC | TGG | GAG | AGA | TCC | CCT | GGC | TTG | CAG | 624 |
| Thr | Arg | Met | Ile | Pro | Arg | Arg | Cys | Trp | Glu | Arg | Ser | Pro | Gly | Leu | Gln | |
| | 625 | | | | | 630 | | | | | 635 | | | | | |

| AAA | ATC | CAG | AAA | ATG | CGG | CAA | CCG | GAA | AGT | ACA | TAA | | | | | 660 |
| Lys | Ile | Gln | Lys | Met | Arg | Gln | Pro | Glu | Ser | Thr | | | | | | |
| 640 | | | | | 645 | | | | | 650 | | | | | | |

( 2 ) INFORMATION FOR SEQ ID NO:6:

( i ) SEQUENCE CHARACTERISTICS:
( A ) LENGTH: 219 amino acids
( B ) TYPE: amino acid
( D ) TOPOLOGY: linear (ii) MOLECULE TYPE: protein (xi) SEQUENCE DESCRIPTION: SEQ ID NO:6:

| Val | Ser | Lys | Arg | Tyr | Phe | Val | Thr | Gly | Thr | Asp | Thr | Glu | Val | Gly | Lys |
|-----|-----|-----|-----|-----|-----|-----|-----|-----|-----|-----|-----|-----|-----|-----|-----|
| 1 | | | | 5 | | | | | 10 | | | | | 15 | |

| Thr | Val | Ala | Ser | Cys | Ala | Leu | Leu | Gln | Ala | Ala | Lys | Arg | Ala | Gly | Tyr |
| | | | 20 | | | | | 25 | | | | | 30 | | |

| Arg | Thr | Ala | Gly | Tyr | Lys | Pro | Val | Ala | Ser | Gly | Ser | Glu | Lys | Thr | Pro |
| | | | 35 | | | | 40 | | | | | 45 | | | |

| Glu | Gly | Leu | Arg | Asn | Ser | Asp | Ala | Leu | Ala | Leu | Gln | Arg | Asn | Ser | Ser |
| | 50 | | | | | 55 | | | | | 60 | | | | |

| Leu | Gln | Leu | Asp | Tyr | Ala | Thr | Val | Asn | Pro | Tyr | Thr | Phe | Ala | Glu | Pro |
| 65 | | | | | 70 | | | | | 75 | | | | | 80 |

| Thr | Ser | Pro | His | Ile | Ile | Ser | Ala | Gln | Glu | Gly | Arg | Pro | Ile | Glu | Ser |
| | | | | 85 | | | | | 90 | | | | | 95 | |

| Leu | Val | Met | Ser | Ala | Gly | Leu | Arg | Ala | Leu | Glu | Gln | Gln | Ala | Asp | Trp |
| | | | 100 | | | | | 105 | | | | | 110 | | |

| Val | Leu | Val | Glu | Gly | Ala | Gly | Gly | Trp | Phe | Thr | Pro | Leu | Ser | Asp | Thr |
| | | 115 | | | | | 120 | | | | | 125 | | | |

| Phe | Thr | Phe | Ala | Asp | Trp | Val | Thr | Gln | Glu | Gln | Leu | Pro | Val | Ile | Leu |
| | 130 | | | | | 135 | | | | | 140 | | | | |

| Val | Val | Gly | Val | Lys | Leu | Gly | Cys | Ile | Asn | His | Ala | Met | Leu | Thr | Ala |
| 145 | | | | | 150 | | | | | 155 | | | | | 160 |

| Gln | Val | Ile | Gln | His | Ala | Gly | Leu | Thr | Leu | Ala | Gly | Trp | Val | Ala | Asn |
| | | | | 165 | | | | | 170 | | | | | 175 | |

| Asp | Val | Thr | Pro | Pro | Gly | Lys | Arg | His | Ala | Glu | Tyr | Met | Thr | Thr | Leu |
| | | | 180 | | | | | 185 | | | | | 190 | | |

| Thr | Arg | Met | Ile | Pro | Arg | Arg | Cys | Trp | Glu | Arg | Ser | Pro | Gly | Leu | Gln |
| | | 195 | | | | | 200 | | | | | 205 | | | |

| Lys | Ile | Gln | Lys | Met | Arg | Gln | Pro | Glu | Ser | Thr |
| | 210 | | | | | 215 | | | | |

(2) INFORMATION FOR SEQ ID NO:7:

(i) SEQUENCE CHARACTERISTICS:
        (A) LENGTH: 1041 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION: 1..1038
        (C) IDENTIFICATION METHOD: experimental
        (D) OTHER INFORMATION: /product="biotin synthase"
           / evidence= EXPERIMENTAL (xi) SEQUENCE DESCRIPTION: SEQ ID NO:7:

| ATG | GCT | CAC | CGC | CCA | CGC | TGG | ACA | TTG | TCG | CAA | GTC | ACA | GAA | TTA | TTT | 48 |
| Met | Ala | His | Arg | Pro | Arg | Trp | Thr | Leu | Ser | Gln | Val | Thr | Glu | Leu | Phe | |
| 220 | | | | 225 | | | | | 230 | | | | | 235 | | |

| GAA | AAA | CCG | TTG | CTG | GAT | CTG | CTG | TTT | GAA | GCG | CAG | CAG | GTG | CAT | CGC | 96 |
| Glu | Lys | Pro | Leu | Leu | Asp | Leu | Leu | Phe | Glu | Ala | Gln | Gln | Val | His | Arg | |
| | | | | 240 | | | | | 245 | | | | | 250 | | |

| CAG | CAT | TTC | GAT | CCT | CGT | CAG | GTG | CAG | GTC | AGC | ACG | TTG | CTG | TCG | ATT | 144 |
| Gln | His | Phe | Asp | Pro | Arg | Gln | Val | Gln | Val | Ser | Thr | Leu | Leu | Ser | Ile | |
| | | | 255 | | | | | 260 | | | | | 265 | | | |

```
AAG  ACC  GGA  GCT  TGT  CCG  GAA  GAT  TGC  AAA  TAC  TGC  CCG  CAA  ACG  TCG      192
Lys  Thr  Gly  Ala  Cys  Pro  Glu  Asp  Cys  Lys  Tyr  Cys  Pro  Gln  Thr  Ser
          270                      275                     280

CGC  TAC  AAA  ACC  GGG  CTG  GAA  GCC  GAG  CGG  TTG  ATG  GAA  GTT  GAA  CAG      240
Arg  Tyr  Lys  Thr  Gly  Leu  Glu  Ala  Glu  Arg  Leu  Met  Glu  Val  Glu  Gln
     285                      290                     295

GTG  CTG  GAG  TCG  GCG  CGC  AAA  GCG  AAA  GCG  GCA  GGA  TCG  ACG  CGC  TTC      288
Val  Leu  Glu  Ser  Ala  Arg  Lys  Ala  Lys  Ala  Ala  Gly  Ser  Thr  Arg  Phe
300                      305                     310                     315

TGT  ATG  GGC  GCG  GCG  TGG  AAG  AAT  CCC  CAC  GAA  CGC  GAT  ATG  CCG  TAC      336
Cys  Met  Gly  Ala  Ala  Trp  Lys  Asn  Pro  His  Glu  Arg  Asp  Met  Pro  Tyr
                    320                      325                     330

CTG  GAA  CAA  ATG  GTG  CAG  GGG  GTA  AAA  GCG  ATG  GGG  CTG  GAG  GCG  TGT      384
Leu  Glu  Gln  Met  Val  Gln  Gly  Val  Lys  Ala  Met  Gly  Leu  Glu  Ala  Cys
               335                      340                     345

ATG  ACG  CTG  GGC  ACG  TTG  AGT  GAA  TCT  CAG  GCG  CAG  CGC  CTC  GCG  AAC      432
Met  Thr  Leu  Gly  Thr  Leu  Ser  Glu  Ser  Gln  Ala  Gln  Arg  Leu  Ala  Asn
          350                      355                     360

GCC  GGG  CTG  GAT  TAC  TAC  AAC  CAC  AAC  CTG  GAC  ACC  TCG  CCG  GAG  TTT      480
Ala  Gly  Leu  Asp  Tyr  Tyr  Asn  His  Asn  Leu  Asp  Thr  Ser  Pro  Glu  Phe
     365                      370                     375

TAC  GGC  AAT  ATC  ATC  ACC  ACA  CGC  ACT  TAT  CAG  GAA  CGC  CTC  GAT  ACG      528
Tyr  Gly  Asn  Ile  Ile  Thr  Thr  Arg  Thr  Tyr  Gln  Glu  Arg  Leu  Asp  Thr
380                      385                     390                     395

CTG  GAA  AAA  GTG  CGC  GAT  GCC  GGG  ATC  AAA  GTC  TGT  TCT  GGC  GGC  ATT      576
Leu  Glu  Lys  Val  Arg  Asp  Ala  Gly  Ile  Lys  Val  Cys  Ser  Gly  Gly  Ile
                    400                      405                     410

GTG  GGC  TTA  GGC  GAA  ACG  GTA  AAA  GAT  CGC  GCC  GGA  TTA  TTG  CTG  CAA      624
Val  Gly  Leu  Gly  Glu  Thr  Val  Lys  Asp  Arg  Ala  Gly  Leu  Leu  Leu  Gln
               415                      420                     425

CTG  GCA  AAC  CTG  CCG  ACG  CCG  CCG  GAA  AGC  GTG  CCA  ATC  AAC  ATG  CTG      672
Leu  Ala  Asn  Leu  Pro  Thr  Pro  Pro  Glu  Ser  Val  Pro  Ile  Asn  Met  Leu
          430                      435                     440

GTG  AAG  GTG  AAA  GGC  ACG  CCG  CTT  GCC  GAT  AAC  GAT  GAT  GTC  GAT  GCC      720
Val  Lys  Val  Lys  Gly  Thr  Pro  Leu  Ala  Asp  Asn  Asp  Asp  Val  Asp  Ala
     445                      450                     455

TTT  GAT  TTT  ATT  CGC  ACC  ATT  GCG  GTC  GCG  CGG  ATC  ATG  ATG  CCA  ACC      768
Phe  Asp  Phe  Ile  Arg  Thr  Ile  Ala  Val  Ala  Arg  Ile  Met  Met  Pro  Thr
460                      465                     470                     475

TCT  TAC  GTG  CGC  CTT  TCT  GCC  GGA  CGC  GAG  CAG  ATG  AAC  GAA  CAG  ACT      816
Ser  Tyr  Val  Arg  Leu  Ser  Ala  Gly  Arg  Glu  Gln  Met  Asn  Glu  Gln  Thr
                    480                      485                     490

CAG  GCG  ATG  TGC  TTT  ATG  GCA  GGC  GCA  AAC  TCG  ATT  TTC  TAC  GGT  TGC      864
Gln  Ala  Met  Cys  Phe  Met  Ala  Gly  Ala  Asn  Ser  Ile  Phe  Tyr  Gly  Cys
               495                      500                     505

AAA  CTG  CTG  ACC  ACG  CCG  AAT  CCG  GAA  GAA  GAT  AAA  GAC  CTG  CAA  CTG      912
Lys  Leu  Leu  Thr  Thr  Pro  Asn  Pro  Glu  Glu  Asp  Lys  Asp  Leu  Gln  Leu
          510                      515                     520

TTC  CGC  AAA  CTG  GGG  CTA  AAT  CCG  CAG  CAA  ACT  GCC  GTG  CTG  GCA  GGG      960
Phe  Arg  Lys  Leu  Gly  Leu  Asn  Pro  Gln  Gln  Thr  Ala  Val  Leu  Ala  Gly
     525                      530                     535

GAT  AAC  GAA  CAA  CAG  CAA  CGT  CTT  GAA  CAG  GCG  CTG  ATG  ACC  CCG  GAC     1008
Asp  Asn  Glu  Gln  Gln  Gln  Arg  Leu  Glu  Gln  Ala  Leu  Met  Thr  Pro  Asp
540                      545                     550                     555

ACC  GAC  GAA  TAT  TAC  AAC  GCG  GCA  GCA  TTA  TGA                              1041
Thr  Asp  Glu  Tyr  Tyr  Asn  Ala  Ala  Ala  Leu
                    560                      565
```

( 2 ) INFORMATION FOR SEQ ID NO:8:

(i) SEQUENCE CHARACTERISTICS:
   (A) LENGTH: 346 amino acids
   (B) TYPE: amino acid
   (D) TOPOLOGY: linear (ii) MOLECULE TYPE: protein (xi) SEQUENCE DESCRIPTION: SEQ ID NO:8:

| Met | Ala | His | Arg | Pro | Arg | Trp | Thr | Leu | Ser | Gln | Val | Thr | Glu | Leu | Phe |
|---|---|---|---|---|---|---|---|---|---|---|---|---|---|---|---|
| 1 | | | | 5 | | | | | 10 | | | | | 15 | |

| Glu | Lys | Pro | Leu | Leu | Asp | Leu | Leu | Phe | Glu | Ala | Gln | Gln | Val | His | Arg |
|---|---|---|---|---|---|---|---|---|---|---|---|---|---|---|---|
| | | | | 20 | | | | 25 | | | | | 30 | | |

| Gln | His | Phe | Asp | Pro | Arg | Gln | Val | Gln | Val | Ser | Thr | Leu | Leu | Ser | Ile |
|---|---|---|---|---|---|---|---|---|---|---|---|---|---|---|---|
| | | 35 | | | | 40 | | | | | 45 | | | | |

| Lys | Thr | Gly | Ala | Cys | Pro | Glu | Asp | Cys | Lys | Tyr | Cys | Pro | Gln | Thr | Ser |
|---|---|---|---|---|---|---|---|---|---|---|---|---|---|---|---|
| | 50 | | | | | 55 | | | | | 60 | | | | |

| Arg | Tyr | Lys | Thr | Gly | Leu | Glu | Ala | Glu | Arg | Leu | Met | Glu | Val | Glu | Gln |
|---|---|---|---|---|---|---|---|---|---|---|---|---|---|---|---|
| 65 | | | | | 70 | | | | | 75 | | | | | 80 |

| Val | Leu | Glu | Ser | Ala | Arg | Lys | Ala | Lys | Ala | Ala | Gly | Ser | Thr | Arg | Phe |
|---|---|---|---|---|---|---|---|---|---|---|---|---|---|---|---|
| | | | | 85 | | | | | 90 | | | | | 95 | |

| Cys | Met | Gly | Ala | Ala | Trp | Lys | Asn | Pro | His | Glu | Arg | Asp | Met | Pro | Tyr |
|---|---|---|---|---|---|---|---|---|---|---|---|---|---|---|---|
| | | | 100 | | | | | 105 | | | | | 110 | | |

| Leu | Glu | Gln | Met | Val | Gln | Gly | Val | Lys | Ala | Met | Gly | Leu | Glu | Ala | Cys |
|---|---|---|---|---|---|---|---|---|---|---|---|---|---|---|---|
| | | | 115 | | | | | 120 | | | | | 125 | | |

| Met | Thr | Leu | Gly | Thr | Leu | Ser | Glu | Ser | Gln | Ala | Gln | Arg | Leu | Ala | Asn |
|---|---|---|---|---|---|---|---|---|---|---|---|---|---|---|---|
| | 130 | | | | | 135 | | | | | 140 | | | | |

| Ala | Gly | Leu | Asp | Tyr | Tyr | Asn | His | Asn | Leu | Asp | Thr | Ser | Pro | Glu | Phe |
|---|---|---|---|---|---|---|---|---|---|---|---|---|---|---|---|
| 145 | | | | | 150 | | | | | 155 | | | | | 160 |

| Tyr | Gly | Asn | Ile | Ile | Thr | Thr | Arg | Thr | Tyr | Gln | Glu | Arg | Leu | Asp | Thr |
|---|---|---|---|---|---|---|---|---|---|---|---|---|---|---|---|
| | | | | 165 | | | | | 170 | | | | | 175 | |

| Leu | Glu | Lys | Val | Arg | Asp | Ala | Gly | Ile | Lys | Val | Cys | Ser | Gly | Gly | Ile |
|---|---|---|---|---|---|---|---|---|---|---|---|---|---|---|---|
| | | | | 180 | | | | | 185 | | | | | 190 | |

| Val | Gly | Leu | Gly | Glu | Thr | Val | Lys | Asp | Arg | Ala | Gly | Leu | Leu | Leu | Gln |
|---|---|---|---|---|---|---|---|---|---|---|---|---|---|---|---|
| | | | 195 | | | | | 200 | | | | | 205 | | |

| Leu | Ala | Asn | Leu | Pro | Thr | Pro | Pro | Glu | Ser | Val | Pro | Ile | Asn | Met | Leu |
|---|---|---|---|---|---|---|---|---|---|---|---|---|---|---|---|
| | 210 | | | | | 215 | | | | | 220 | | | | |

| Val | Lys | Val | Lys | Gly | Thr | Pro | Leu | Ala | Asp | Asn | Asp | Asp | Val | Asp | Ala |
|---|---|---|---|---|---|---|---|---|---|---|---|---|---|---|---|
| 225 | | | | | 230 | | | | | 235 | | | | | 240 |

| Phe | Asp | Phe | Ile | Arg | Thr | Ile | Ala | Val | Ala | Arg | Ile | Met | Met | Pro | Thr |
|---|---|---|---|---|---|---|---|---|---|---|---|---|---|---|---|
| | | | | 245 | | | | | 250 | | | | | 255 | |

| Ser | Tyr | Val | Arg | Leu | Ser | Ala | Gly | Arg | Glu | Gln | Met | Asn | Glu | Gln | Thr |
|---|---|---|---|---|---|---|---|---|---|---|---|---|---|---|---|
| | | | 260 | | | | | 265 | | | | | 270 | | |

| Gln | Ala | Met | Cys | Phe | Met | Ala | Gly | Ala | Asn | Ser | Ile | Phe | Tyr | Gly | Cys |
|---|---|---|---|---|---|---|---|---|---|---|---|---|---|---|---|
| | | 275 | | | | | 280 | | | | | 285 | | | |

| Lys | Leu | Leu | Thr | Thr | Pro | Asn | Pro | Glu | Glu | Asp | Lys | Asp | Leu | Gln | Leu |
|---|---|---|---|---|---|---|---|---|---|---|---|---|---|---|---|
| | 290 | | | | | 295 | | | | | 300 | | | | |

| Phe | Arg | Lys | Leu | Gly | Leu | Asn | Pro | Gln | Gln | Thr | Ala | Val | Leu | Ala | Gly |
|---|---|---|---|---|---|---|---|---|---|---|---|---|---|---|---|
| 305 | | | | | 310 | | | | | 315 | | | | | 320 |

| Asp | Asn | Glu | Gln | Gln | Gln | Arg | Leu | Glu | Gln | Ala | Leu | Met | Thr | Pro | Asp |
|---|---|---|---|---|---|---|---|---|---|---|---|---|---|---|---|
| | | | | 325 | | | | | 330 | | | | | 335 | |

| Thr | Asp | Glu | Tyr | Tyr | Asn | Ala | Ala | Ala | Leu |
|---|---|---|---|---|---|---|---|---|---|
| | | | 340 | | | | | 345 | |

(2) INFORMATION FOR SEQ ID NO:9:

(i) SEQUENCE CHARACTERISTICS:
      (A) LENGTH: 44 base pairs

-continued

```
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide primer for
              PCR of bioA gene"

( i i i ) HYPOTHETICAL: NO ( x i ) SEQUENCE DESCRIPTION: SEQ ID NO:9:
```

GGAATTCAGA AGACGACATG ACAACGGACG ATCTTGCCTT TGAC                                44

( 2 ) INFORMATION FOR SEQ ID NO:10:

```
    ( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide primer for
              PCR of bioA gene"

( i i i ) HYPOTHETICAL: NO ( x i ) SEQUENCE DESCRIPTION: SEQ ID NO:10:
```

GGAATTCAGG TACCATTTAT TGGCAAAAAA ATGTTTCATC CTGTAC                              46

( 2 ) INFORMATION FOR SEQ ID NO:11:

```
    ( i ) SEQUENCE CHARACTERISTICS:
        ( A ) LENGTH: 756 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 1..753
        ( C ) IDENTIFICATION METHOD: experimental
        ( D ) OTHER INFORMATION: /product="bioC gene product; functions
              biotin pathway before pimelic acid"
              / evidence= EXPERIMENTAL ( x i ) SEQUENCE DESCRIPTION: SEQ ID NO:11:
```

| ATG | GCA | ACG | GTT | AAT | AAA | CAA | GCC | ATT | GCA | GCG | GCA | TTT | GGT | CGG | GCA | 48 |
| Met | Ala | Thr | Val | Asn | Lys | Gln | Ala | Ile | Ala | Ala | Ala | Phe | Gly | Arg | Ala | |
| | | | 350 | | | | 355 | | | | | 360 | | | | |

| GCC | GCA | CAC | TAT | GAG | CAA | CAT | GCA | GAT | CTA | CAG | CGC | CAG | AGT | GCT | GAC | 96 |
| Ala | Ala | His | Tyr | Glu | Gln | His | Ala | Asp | Leu | Gln | Arg | Gln | Ser | Ala | Asp | |
| | | 365 | | | | 370 | | | | | 375 | | | | | |

| GCC | TTA | CTG | GCA | ATG | CTT | CCA | CAG | CGT | AAA | TAC | ACC | CAC | GTA | CTG | GAC | 144 |
| Ala | Leu | Leu | Ala | Met | Leu | Pro | Gln | Arg | Lys | Tyr | Thr | His | Val | Leu | Asp | |
| | 380 | | | | 385 | | | | | 390 | | | | | | |

| GCG | GGT | TGT | GGA | CCT | GGC | TGG | ATG | AGC | CGC | CAC | TGG | CGG | GAA | CGT | CAC | 192 |
| Ala | Gly | Cys | Gly | Pro | Gly | Trp | Met | Ser | Arg | His | Trp | Arg | Glu | Arg | His | |
| 395 | | | | 400 | | | | | 405 | | | | | | 410 | |

| GCG | CAG | GTG | ACG | GCC | TTA | GAT | CTC | TCG | CCG | CCA | ATG | CTT | GTT | CAG | GCA | 240 |
| Ala | Gln | Val | Thr | Ala | Leu | Asp | Leu | Ser | Pro | Pro | Met | Leu | Val | Gln | Ala | |
| | | | | 415 | | | | 420 | | | | | 425 | | | |

| CGC | CAG | AAG | GAT | GCC | GCA | GAC | CAT | TAT | CTG | GCG | GGA | GAT | ATC | GAA | TCC | 288 |
| Arg | Gln | Lys | Asp | Ala | Ala | Asp | His | Tyr | Leu | Ala | Gly | Asp | Ile | Glu | Ser | |
| | | | 430 | | | | 435 | | | | | 440 | | | | |

| | | | | | | | | | | | | | | | | |
|---|---|---|---|---|---|---|---|---|---|---|---|---|---|---|---|---|
| CTG | CCG | TTA | GCG | ACT | GCG | ACG | TTC | GAT | CTT | GCA | TGG | AGC | AAT | CTC | GCA | 336 |
| Leu | Pro | Leu | Ala | Thr | Ala | Thr | Phe | Asp | Leu | Ala | Trp | Ser | Asn | Leu | Ala | |
| | | 445 | | | | 450 | | | | | 455 | | | | | |
| GTG | CAG | TGG | TGC | GGT | AAT | TTA | TCC | ACG | GCA | CTC | CGC | GAG | CTG | TAT | CGG | 384 |
| Val | Gln | Trp | Cys | Gly | Asn | Leu | Ser | Thr | Ala | Leu | Arg | Glu | Leu | Tyr | Arg | |
| 460 | | | | | 465 | | | | | | 470 | | | | | |
| GTG | GTG | CGC | CCC | AAA | GGC | GTG | GTC | GCG | TTT | ACC | ACG | CTG | GTG | CAG | GGA | 432 |
| Val | Val | Arg | Pro | Lys | Gly | Val | Val | Ala | Phe | Thr | Thr | Leu | Val | Gln | Gly | |
| 475 | | | | | 480 | | | | | 485 | | | | | 490 | |
| TCG | TTA | CCC | GAA | CGT | CAT | CAG | GCG | TGG | CAG | GCG | GTG | GAC | GAG | CGT | CCG | 480 |
| Ser | Leu | Pro | Glu | Arg | His | Gln | Ala | Trp | Gln | Ala | Val | Asp | Glu | Arg | Pro | |
| | | | | 495 | | | | 500 | | | | | 505 | | | |
| CAT | GCT | AAT | CGC | TTT | TTA | CCG | CCA | GAT | GAA | ATC | GAA | CAG | TCG | CTG | AAC | 528 |
| His | Ala | Asn | Arg | Phe | Leu | Pro | Pro | Asp | Glu | Ile | Glu | Gln | Ser | Leu | Asn | |
| | | | 510 | | | | | 515 | | | | | 520 | | | |
| GGC | GTG | CAT | TAT | CAA | CAT | CAT | ATT | CAG | CCC | ATC | ACG | CTG | TGG | TTT | GAT | 576 |
| Gly | Val | His | Tyr | Gln | His | His | Ile | Gln | Pro | Ile | Thr | Leu | Trp | Phe | Asp | |
| | | 525 | | | | | 530 | | | | | 535 | | | | |
| GAT | GCG | CTC | AGT | GCC | ATG | CGT | TCG | CTG | AAA | GGC | ATC | GGT | GCC | ACG | CAT | 624 |
| Asp | Ala | Leu | Ser | Ala | Met | Arg | Ser | Leu | Lys | Gly | Ile | Gly | Ala | Thr | His | |
| | 540 | | | | | 545 | | | | | 550 | | | | | |
| CTT | CAT | GAA | GGG | CGC | GAC | CCG | CGA | ATA | TTA | ACG | CGT | TCG | CAG | TTG | CAG | 672 |
| Leu | His | Glu | Gly | Arg | Asp | Pro | Arg | Ile | Leu | Thr | Arg | Ser | Gln | Leu | Gln | |
| 555 | | | | | 560 | | | | | 565 | | | | | 570 | |
| CGA | TTG | CAA | CTG | GCC | TGG | CCG | CAA | CAG | CAG | GGG | CGA | TAT | CCT | CTG | ACG | 720 |
| Arg | Leu | Gln | Leu | Ala | Trp | Pro | Gln | Gln | Gln | Gly | Arg | Tyr | Pro | Leu | Thr | |
| | | | | 575 | | | | | 580 | | | | | 585 | | |
| TAT | CAT | CTT | TTT | TTG | GGA | GTG | ATT | GCT | CGT | GAG | TAA | | | | | 756 |
| Tyr | His | Leu | Phe | Leu | Gly | Val | Ile | Ala | Arg | Glu | | | | | | |
| | | | 590 | | | | 595 | | | | | | | | | |

( 2 ) INFORMATION FOR SEQ ID NO:12:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Met | Ala | Thr | Val | Asn | Lys | Gln | Ala | Ile | Ala | Ala | Phe | Gly | Arg | Ala |
| 1 | | | | 5 | | | | | 10 | | | | | 15 |
| Ala | Ala | His | Tyr | Glu | Gln | His | Ala | Asp | Leu | Gln | Arg | Gln | Ser | Ala | Asp |
| | | | 20 | | | | | 25 | | | | | 30 | | |
| Ala | Leu | Leu | Ala | Met | Leu | Pro | Gln | Arg | Lys | Tyr | Thr | His | Val | Leu | Asp |
| | | | 35 | | | | | 40 | | | | | 45 | | |
| Ala | Gly | Cys | Gly | Pro | Gly | Trp | Met | Ser | Arg | His | Trp | Arg | Glu | Arg | His |
| | 50 | | | | | 55 | | | | | 60 | | | | |
| Ala | Gln | Val | Thr | Ala | Leu | Asp | Leu | Ser | Pro | Pro | Met | Leu | Val | Gln | Ala |
| 65 | | | | | 70 | | | | | 75 | | | | | 80 |
| Arg | Gln | Lys | Asp | Ala | Ala | Asp | His | Tyr | Leu | Ala | Gly | Asp | Ile | Glu | Ser |
| | | | | 85 | | | | | 90 | | | | | 95 | |
| Leu | Pro | Leu | Ala | Thr | Ala | Thr | Phe | Asp | Leu | Ala | Trp | Ser | Asn | Leu | Ala |
| | | | | 100 | | | | | 105 | | | | | 110 | |
| Val | Gln | Trp | Cys | Gly | Asn | Leu | Ser | Thr | Ala | Leu | Arg | Glu | Leu | Tyr | Arg |
| | | | 115 | | | | | 120 | | | | | 125 | | |
| Val | Val | Arg | Pro | Lys | Gly | Val | Val | Ala | Phe | Thr | Thr | Leu | Val | Gln | Gly |
| | | | 130 | | | | | 135 | | | | | 140 | | |
| Ser | Leu | Pro | Glu | Arg | His | Gln | Ala | Trp | Gln | Ala | Val | Asp | Glu | Arg | Pro |

```
                        145                 150                 155                 160
His  Ala  Asn  Arg  Phe  Leu  Pro  Pro  Asp  Glu  Ile  Glu  Gln  Ser  Leu  Asn
                    165                 170                 175

Gly  Val  His  Tyr  Gln  His  His  Ile  Gln  Pro  Ile  Thr  Leu  Trp  Phe  Asp
               180                 185                      190

Asp  Ala  Leu  Ser  Ala  Met  Arg  Ser  Leu  Lys  Gly  Ile  Gly  Ala  Thr  His
          195                      200                      205

Leu  His  Glu  Gly  Arg  Asp  Pro  Arg  Ile  Leu  Thr  Arg  Ser  Gln  Leu  Gln
     210                      215                 220

Arg  Leu  Gln  Leu  Ala  Trp  Pro  Gln  Gln  Gln  Gly  Arg  Tyr  Pro  Leu  Thr
225                      230                 235                           240

Tyr  His  Leu  Phe  Leu  Gly  Val  Ile  Ala  Arg  Glu
               245                           250
```

( 2 ) INFORMATION FOR SEQ ID NO:13:

( i ) SEQUENCE CHARACTERISTICS:
        ( A ) LENGTH: 1351 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 59..1192
        ( D ) OTHER INFORMATION: /product="Arabidopsis biotin synthase enzyme"

( x i ) SEQUENCE DESCRIPTION: SEQ ID NO:13:

```
GGCACGAGCT  CATTTCTTCT  TCTTCTTCTT  TTTCCACATT  TTCTGATTAG  CAGATCAA                    58

ATG  ATG  CTT  GTT  CGA  TCT  GTA  TTT  CGA  TCT  CAG  TTG  CGA  CCC  TCT  GTC         106
Met  Met  Leu  Val  Arg  Ser  Val  Phe  Arg  Ser  Gln  Leu  Arg  Pro  Ser  Val
 1              5                        10                       15

TCG  GGT  GGT  CTG  CAA  TCT  GCT  TCT  TGC  TAT  TCT  TCA  TTA  TCT  GCT  GCT         154
Ser  Gly  Gly  Leu  Gln  Ser  Ala  Ser  Cys  Tyr  Ser  Ser  Leu  Ser  Ala  Ala
                20                        25                       30

TCA  GCT  GAA  GCT  GAG  AGG  ACT  ATC  AGA  GAA  GGT  CCC  AGA  AAC  GAT  TGG         202
Ser  Ala  Glu  Ala  Glu  Arg  Thr  Ile  Arg  Glu  Gly  Pro  Arg  Asn  Asp  Trp
          35                        40                       45

AGT  AGA  GAT  GAA  ATC  AAG  TCT  GTT  TAT  GAT  TCT  CCT  CTT  CTT  GAC  CTC         250
Ser  Arg  Asp  Glu  Ile  Lys  Ser  Val  Tyr  Asp  Ser  Pro  Leu  Leu  Asp  Leu
     50                        55                       60

CTC  TTC  CAT  GGA  GCT  CAG  GTT  CAT  AGA  CAT  GTT  CAT  AAC  TTC  AGG  GAG         298
Leu  Phe  His  Gly  Ala  Gln  Val  His  Arg  His  Val  His  Asn  Phe  Arg  Glu
65                       70                        75                            80

GTA  CAA  CAA  TGT  ACC  CTC  CTC  TCC  ATA  AAG  ACT  GGT  GGC  TGT  AGT  GAA         346
Val  Gln  Gln  Cys  Thr  Leu  Leu  Ser  Ile  Lys  Thr  Gly  Gly  Cys  Ser  Glu
                    85                        90                       95

GAC  TGT  TCA  TAT  TGT  CCT  CAG  TCT  TCG  AGA  TAT  AGC  ACT  GGA  GTT  AAG         394
Asp  Cys  Ser  Tyr  Cys  Pro  Gln  Ser  Ser  Arg  Tyr  Ser  Thr  Gly  Val  Lys
                    100                      105                      110

GCA  CAA  AGA  CTC  ATG  TCT  AAG  GAC  GCT  GTC  ATT  GAT  GCT  GCT  AAG  AAG         442
Ala  Gln  Arg  Leu  Met  Ser  Lys  Asp  Ala  Val  Ile  Asp  Ala  Ala  Lys  Lys
          115                      120                      125

GCA  AAA  GAA  GCT  GGG  AGC  ACA  CGT  TTT  TGC  ATG  GGT  GCT  GCT  TGG  CGA         490
Ala  Lys  Glu  Ala  Gly  Ser  Thr  Arg  Phe  Cys  Met  Gly  Ala  Ala  Trp  Arg
     130                      135                      140

GAT  ACA  ATT  GGA  CGG  AAA  ACC  AAC  TTC  AGC  CAG  ATT  CTT  GAA  TAC  ATC         538
```

```
Asp  Thr  Ile  Gly  Arg  Lys  Thr  Asn  Phe  Ser  Gln  Ile  Leu  Glu  Tyr  Ile
145            150                      155                      160

AAA  GAA  ATA  AGA  GGC  ATG  GGG  ATG  GAA  GTT  TGC  TGC  ACC  TTA  GGC  ATG        586
Lys  Glu  Ile  Arg  Gly  Met  Gly  Met  Glu  Val  Cys  Cys  Thr  Leu  Gly  Met
               165                      170                      175

ATT  GAG  AAA  CAA  CAA  GCA  CTA  GAG  CTA  AAG  AAG  GCT  GGC  CTC  ACT  GCT        634
Ile  Glu  Lys  Gln  Gln  Ala  Leu  Glu  Leu  Lys  Lys  Ala  Gly  Leu  Thr  Ala
               180                      185                      190

TAT  AAC  CAC  AAT  CTT  GAT  ACT  TCA  AGA  GAG  TAC  TAC  CCA  AAC  GTC  ATC        682
Tyr  Asn  His  Asn  Leu  Asp  Thr  Ser  Arg  Glu  Tyr  Tyr  Pro  Asn  Val  Ile
               195                      200                      205

ACT  ACT  AGA  AGT  TAT  GAC  GAT  CGC  CTT  GAA  ACT  CTT  AGC  CAT  GTT  CGT        730
Thr  Thr  Arg  Ser  Tyr  Asp  Asp  Arg  Leu  Glu  Thr  Leu  Ser  His  Val  Arg
     210                      215                      220

GAT  GCT  GGA  ATC  AAC  GTT  TGT  TCA  GGA  GGA  ATC  ATA  GGG  CTT  GGT  GAG        778
Asp  Ala  Gly  Ile  Asn  Val  Cys  Ser  Gly  Gly  Ile  Ile  Gly  Leu  Gly  Glu
225                 230                      235                      240

GCA  GAG  GAA  GAC  AGA  ATA  GGT  TTA  TTA  CAC  ACG  CTG  GCA  ACA  CTT  CCT        826
Ala  Glu  Glu  Asp  Arg  Ile  Gly  Leu  Leu  His  Thr  Leu  Ala  Thr  Leu  Pro
               245                      250                      255

TCT  CAC  CCT  GAG  AGT  GTT  CCC  ATT  AAT  GCT  CTA  CTT  GCA  GTG  AAA  GGC        874
Ser  His  Pro  Glu  Ser  Val  Pro  Ile  Asn  Ala  Leu  Leu  Ala  Val  Lys  Gly
               260                      265                      270

ACT  CCT  CTT  GAA  GAC  CAG  AAG  CCA  GTT  GAG  ATA  TGG  GAG  ATG  ATC  AGG        922
Thr  Pro  Leu  Glu  Asp  Gln  Lys  Pro  Val  Glu  Ile  Trp  Glu  Met  Ile  Arg
          275                      280                      285

ATG  ATT  GGA  ACC  GCA  CGT  ATT  GTA  ATG  CCA  AAA  GCG  ATG  GTG  AGA  CTG        970
Met  Ile  Gly  Thr  Ala  Arg  Ile  Val  Met  Pro  Lys  Ala  Met  Val  Arg  Leu
     290                      295                      300

TCT  GCT  GGT  AGA  GTC  CGG  TTC  TCA  ATG  TCC  GAA  CAA  GCT  CTC  TGT  TTC       1018
Ser  Ala  Gly  Arg  Val  Arg  Phe  Ser  Met  Ser  Glu  Gln  Ala  Leu  Cys  Phe
305                      310                      315                      320

CTT  GCT  GGT  GCA  AAC  TCT  ATC  TTC  ACC  GGA  GAG  AAG  CTT  TTA  ACC  ACA       1066
Leu  Ala  Gly  Ala  Asn  Ser  Ile  Phe  Thr  Gly  Glu  Lys  Leu  Leu  Thr  Thr
                    325                      330                      335

CCA  AAC  AAT  GAT  TTT  GAC  GCT  GAC  CAG  CTC  ATG  TTC  AAG  ACA  TTA  GGC       1114
Pro  Asn  Asn  Asp  Phe  Asp  Ala  Asp  Gln  Leu  Met  Phe  Lys  Thr  Leu  Gly
               340                      345                      350

CTC  ATT  CCT  AAA  CCG  CCA  AGT  TTC  TCT  GGA  GAT  GAT  TCT  GAA  TCA  GAA       1162
Leu  Ile  Pro  Lys  Pro  Pro  Ser  Phe  Ser  Gly  Asp  Asp  Ser  Glu  Ser  Glu
          355                      360                      365

AAC  TGC  GAG  AAA  GTT  GCT  TCC  GCT  TCT  CAC  TAATATCATT  ATCCACTTTT            1212
Asn  Cys  Glu  Lys  Val  Ala  Ser  Ala  Ser  His
     370                      375

TTTTTGTTT   GGAGTCGGGA   CACTATAGAG   CAGTCCCTTT   TACTATGTAG   CATGGTTTGA           1272

CGATTTTGTG   ATATCATTTT   TCGTTAATCG   TTATTCGAAG   ATGTCTAGAT   TTCTCATCTG          1332

AAAAAAAAAA   AAAAAAAA                                                               1351

( 2 ) INFORMATION FOR SEQ ID NO:14:

( i ) SEQUENCE CHARACTERISTICS:
                ( A ) LENGTH: 378 amino acids
                ( B ) TYPE: amino acid
                ( D ) TOPOLOGY: linear ( i i ) MOLECULE TYPE: protein ( x i ) SEQUENCE DESCRIPTION: SEQ ID NO:14:

Met  Met  Leu  Val  Arg  Ser  Val  Phe  Arg  Ser  Gln  Leu  Arg  Pro  Ser  Val
1              5                        10                       15
```

| | | | | | | | | | | | | | | |
|---|---|---|---|---|---|---|---|---|---|---|---|---|---|---|
| Ser | Gly | Gly | Leu 20 | Gln | Ser | Ala | Ser | Cys 25 | Tyr | Ser | Ser | Leu | Ser 30 | Ala | Ala |
| Ser | Ala | Glu 35 | Ala | Glu | Arg | Thr | Ile 40 | Arg | Glu | Gly | Pro | Arg 45 | Asn | Asp | Trp |
| Ser | Arg 50 | Asp | Glu | Ile | Lys | Ser 55 | Val | Tyr | Asp | Ser | Pro 60 | Leu | Leu | Asp | Leu |
| Leu 65 | Phe | His | Gly | Ala | Gln 70 | Val | His | Arg | His | Val 75 | His | Asn | Phe | Arg | Glu 80 |
| Val | Gln | Gln | Cys | Thr 85 | Leu | Leu | Ser | Ile | Lys 90 | Thr | Gly | Gly | Cys | Ser 95 | Glu |
| Asp | Cys | Ser | Tyr 100 | Cys | Pro | Gln | Ser | Ser 105 | Arg | Tyr | Ser | Thr | Gly 110 | Val | Lys |
| Ala | Gln | Arg 115 | Leu | Met | Ser | Lys | Asp 120 | Ala | Val | Ile | Asp | Ala 125 | Ala | Lys | Lys |
| Ala | Lys 130 | Glu | Ala | Gly | Ser | Thr 135 | Arg | Phe | Cys | Met | Gly 140 | Ala | Ala | Trp | Arg |
| Asp 145 | Thr | Ile | Gly | Arg | Lys 150 | Thr | Asn | Phe | Ser | Gln 155 | Ile | Leu | Glu | Tyr | Ile 160 |
| Lys | Glu | Ile | Arg | Gly 165 | Met | Gly | Met | Glu | Val 170 | Cys | Cys | Thr | Leu | Gly 175 | Met |
| Ile | Glu | Lys | Gln 180 | Gln | Ala | Leu | Glu | Leu 185 | Lys | Lys | Ala | Gly | Leu 190 | Thr | Ala |
| Tyr | Asn | His 195 | Asn | Leu | Asp | Thr | Ser 200 | Arg | Glu | Tyr | Tyr | Pro 205 | Asn | Val | Ile |
| Thr | Thr 210 | Arg | Ser | Tyr | Asp | Arg 215 | Leu | Glu | Thr | Leu 220 | Ser | His | Val | Arg |
| Asp 225 | Ala | Gly | Ile | Asn | Val 230 | Cys | Ser | Gly | Gly | Ile 235 | Ile | Gly | Leu | Gly | Glu 240 |
| Ala | Glu | Glu | Asp | Arg 245 | Ile | Gly | Leu | Leu | His 250 | Thr | Leu | Ala | Thr | Leu 255 | Pro |
| Ser | His | Pro | Glu 260 | Ser | Val | Pro | Ile | Asn 265 | Ala | Leu | Leu | Ala | Val 270 | Lys | Gly |
| Thr | Pro | Leu 275 | Glu | Asp | Gln | Lys | Pro 280 | Val | Glu | Ile | Trp | Glu 285 | Met | Ile | Arg |
| Met | Ile 290 | Gly | Thr | Ala | Arg | Ile 295 | Val | Met | Pro | Lys | Ala 300 | Met | Val | Arg | Leu |
| Ser 305 | Ala | Gly | Arg | Val | Arg 310 | Phe | Ser | Met | Ser | Glu 315 | Gln | Ala | Leu | Cys | Phe 320 |
| Leu | Ala | Gly | Ala | Asn 325 | Ser | Ile | Phe | Thr | Gly 330 | Glu | Lys | Leu | Leu | Thr 335 | Thr |
| Pro | Asn | Asn | Asp 340 | Phe | Asp | Ala | Asp | Gln 345 | Leu | Met | Phe | Lys | Thr 350 | Leu | Gly |
| Leu | Ile | Pro 355 | Lys | Pro | Pro | Ser | Phe 360 | Ser | Gly | Asp | Asp | Ser 365 | Glu | Ser | Glu |
| Asn | Cys 370 | Glu | Lys | Val | Ala | Ser 375 | Ala | Ser | His | | | | | | |

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Forward PCR Primer DP199 used in Example 9"

(x i) SEQUENCE DESCRIPTION: SEQ ID NO:15:

GATCGAATTC GCTGCTCTCT AAAAAGTCAT G        31

(2) INFORMATION FOR SEQ ID NO:16:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Reverse PCR primer DP200
            used in Example 9"

(x i) SEQUENCE DESCRIPTION: SEQ ID NO:16:

CTCGAGATCG TACGCCATGG TTTTGCTATT TGTGTTTGTA TTC        43

(2) INFORMATION FOR SEQ ID NO:17:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Forward PCR primer DP201
            used in Example 9"

(x i) SEQUENCE DESCRIPTION: SEQ ID NO:17:

CCATTGCGTA CGATCTCGAG ACTTAGTATG TATTTGTATT TG        42

(2) INFORMATION FOR SEQ ID NO:18:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Reverse PCR primer DP202
            used in Example 9"

(x i) SEQUENCE DESCRIPTION: SEQ ID NO:18:

GATCGGTACC GAATTCGTAC CCACTGGATT TTGG        34

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Forward PCR primer DP205
            used in Example 9"

(x i) SEQUENCE DESCRIPTION: SEQ ID NO:19:

GTCACCATGG CTCACCGCCC ACGC        24

(2) INFORMATION FOR SEQ ID NO:20:

(i) SEQUENCE CHARACTERISTICS:
        (A) LENGTH: 29 base pairs
        (B) TYPE: nucleic acid ( C ) STRANDEDNESS: single
( D ) TOPOLOGY: linear ( i i ) MOLECULE TYPE: other nucleic acid
( A ) DESCRIPTION: /desc = "Reverse PCR primer DP206 used in Example 9"

( x i ) SEQUENCE DESCRIPTION: SEQ ID NO:20:

GGATCTCGAG TCATAATGCT GCCGCGTTG 29